(12) United States Patent
Garcia et al.

(10) Patent No.: US 9,970,897 B2
(45) Date of Patent: May 15, 2018

(54) CHEMICAL SENSORS AND METHODS FOR MAKING AND USING THE SAME

(75) Inventors: Michael A. Garcia, Durham, NC (US); Scott D. Wolter, Durham, NC (US); April S. Brown, Durham, NC (US); William V. Lampert, Durham, NC (US)

(73) Assignee: Duke University, Durham, NC (US)

( * ) Notice: Subject to any disclaimer, the term of this patent is extended or adjusted under 35 U.S.C. 154(b) by 667 days.

(21) Appl. No.: 12/999,262

(22) PCT Filed: Jun. 16, 2009

(86) PCT No.: PCT/US2009/047546
§ 371 (c)(1),
(2), (4) Date: Apr. 29, 2011

(87) PCT Pub. No.: WO2010/005738
PCT Pub. Date: Jan. 14, 2010

(65) Prior Publication Data
US 2011/0199102 A1    Aug. 18, 2011

Related U.S. Application Data

(60) Provisional application No. 61/129,273, filed on Jun. 16, 2008, provisional application No. 61/129,274, (Continued)

(51) Int. Cl.
*G01N 27/414* (2006.01)
(52) U.S. Cl.
CPC ..... *G01N 27/4148* (2013.01); *G01N 27/4145* (2013.01)

(58) Field of Classification Search
CPC .................. G01N 27/4148; G01N 27/4145
See application file for complete search history.

(56) References Cited

U.S. PATENT DOCUMENTS 5,603,820 A    2/1997  Malinski et al.
5,674,700 A   10/1997  Maurel
(Continued)

FOREIGN PATENT DOCUMENTS

EP    1801886     6/2007
WO   93/08464    4/1993
(Continued)

OTHER PUBLICATIONS

United States Patent Office Action for U.S. Appl. No. 13/201,181 dated Oct. 19, 2012 (13 pages).
(Continued)

*Primary Examiner* — Melanie Yu Brown
(74) *Attorney, Agent, or Firm* — Michael Best & Friedrich LLP

(57) ABSTRACT

A van der Pauw (VDP) sensor comprising an electronic circuit electrically coupled to a surface, the surface comprising a type III-V material, and the electronic circuit measuring a sheet resistivity of the surface using a VDP technique. The VDP sensor may further comprise a macromolecule, such as a porphyrin, an oligonucleotide, a protein, a polymer or a combination thereof in contact with the surface. The VDP sensors may be arranged in an array of similar or different sensors. An electronic circuit electrically coupled to a type III-V material having a two-dimensional electron gas, such as InAs or InN, the electronic circuit measuring an electrical property of the type III-V material having a two-dimensional electron gas.

16 Claims, 14 Drawing Sheets

Related U.S. Application Data filed on Jun. 16, 2008, provisional application No. 61/136,072, filed on Aug. 11, 2008, provisional application No. 61/136,073, filed on Aug. 11, 2008.

(56) References Cited

U.S. PATENT DOCUMENTS

| | | |
|---|---|---|
| 6,433,356 B1 | 8/2002 | Cahen et al. |
| 6,716,620 B2 | 4/2004 | Bashir et al. |
| 7,361,946 B2 | 4/2008 | Johnson et al. |
| 7,504,658 B2 * | 3/2009 | Kunze et al. ............ 257/48 |
| 7,868,354 B2 | 1/2011 | Garcia et al. |
| 8,828,713 B2 | 9/2014 | Ren et al. |
| 2003/0036054 A1 | 2/2003 | Ladisch et al. |
| 2003/0059954 A1 | 3/2003 | Vikholm et al. |
| 2003/0138829 A1 | 7/2003 | Unger et al. |
| 2004/0072360 A1 | 4/2004 | Naaman et al. |
| 2004/0115711 A1 * | 6/2004 | Su et al. ............ 435/6 |
| 2004/0157281 A1 | 8/2004 | Hulkower et al. |
| 2004/0159836 A1 * | 8/2004 | Sugimoto et al. ............ 257/40 |
| 2005/0097941 A1 | 5/2005 | Sandvik et al. |
| 2006/0267570 A1 | 11/2006 | Arkin |
| 2007/0176211 A1 * | 8/2007 | Kunze et al. ............ 257/232 |
| 2007/0264623 A1 * | 11/2007 | Wang et al. ............ 435/4 |
| 2009/0057650 A1 | 3/2009 | Lieber et al. |
| 2009/0085071 A1 * | 4/2009 | Brongersma ...... G01N 27/4146 257/253 |
| 2010/0188069 A1 * | 7/2010 | Ren et al. ............ 324/71.5 |
| 2011/0068372 A1 * | 3/2011 | Ren ............ G01N 27/414 257/194 |
| 2012/0058488 A1 | 3/2012 | Sheppard et al. |
| 2013/0288378 A1 | 10/2013 | Gu et al. |

FOREIGN PATENT DOCUMENTS

| | | |
|---|---|---|
| WO | WO 2010/005738 | 1/2010 |
| WO | 2011/046858 | 4/2011 |
| WO | 2013/039819 | 3/2013 |

OTHER PUBLICATIONS

United States Patent Office Action for U.S. Appl. No. 12/948,946 dated Aug. 27, 2012 (8 pages).
United States Patent Office Action for U.S. Appl. No. 11/937,375 dated Aug. 24, 2009 (7 pages).
United States Patent Office Action for U.S. Appl. No. 11/937,375 dated Apr. 27, 2010 (8 pages).
United States Patent Office Action for U.S. Appl. No. 11/937,375 dated Jun. 17, 2010 (4 pages).
United States Patent Office Action for U.S. Appl. No. 11/937,375 dated Jul. 9, 2010 (5 pages).
Invitation to Pay Additional Fees for Application No. PCT/US2009/047546 dated Jun. 24, 2009 (2 pages).
International Search Report and Written Opinion for Application No. PCT/US2010/023917 dated Jun. 14, 2010 (17 pages).
Addison, A.W. et al., "Hemoglobin: autoreduction and spectroscopy," Biochem. (1986) 25:4104-4113.
Angelo et al., "Interaction of NO with hemoglobin: from microbes to man," Methods Enzym. (2008) 436:125-158.
Ashkenasy, G. et al., "Molecular engineering of semiconductor surfaces and devices," Acc. Chem. Res. (2002) 35:121-128.
Battut, V. et al., "Gas sensitivity of InP epitaxial thin layers," Sensors and Actuators B (1997) 44:503-506.
Bayer, M. et al., "Theoretical study of electrolyte gate AlGaN/GaN field deffect transistors," Appl. Phys. Lett. (2005) 97:033703, 6 pages.
Bedioui, F. et al., "Electtrochemical nitric oxide sensors for biological samples—principle, selected examples and application," Electroanalysis (2003) 15:5-18.
Bell, G.R. et al., "Accumulation layer profiles at InAs polar surfaces." Applied Phys. Lett. (1997) 71:3688-3690.
Cahen, D. et al., "The cooperative molecular field effect," Adv. Funct. Mater. (2005) 15:1571-1578.
Crawford, J.H. et al., "Transduction of NO-bioactivity by the red blood cell in sepsis: novel mechanisms of vasodilation during acute inflammatory disease," Blood (2004) 105:1375-1382.
Culotta, E. et al., "No news is good news," Science (1992) 258(5090):1862-1865.
Eickhoff, M. et al., "Electronics and sensors-based on pyroelectric AlGaN/GaN heterostructures; Part B: sensor applications," Phys. Stat. Sol. (2003) 6:1908-1918.
Flechtner, K. et al., "No-induced reversible switching of the electronic interaction between a porphyrin-coordinated cobalt ion and a silver surface," J. Am. Chem. Soc. (2007) 129:12110-12111.
Garcia, M. et al., "Functionalization and characterization of InAs and InP surfaces with hemin," J. Vac. Sci. Technol. (2007) 25:1504-1510.
Garcia, M.A. et al., "Comparison of functionalized III-V semiconductor response for nitric oxide," Sensor Letters (2008) 6:627-634.
Gaston, B., "Nitric oxide and thiol groups," Biochim Biophys. Acta (1999) 1411:323-333.
Gomez, R. et al "Instrumentation system for in vivo organ studies," IEEE (2001) 1:26-1624.
Gow, A.J. et al., "Reactions between nitrie oxide and haemoglobin under physiological conditions," Nature (1998) 391:169-173.
Gow, A.J. et al., "The oxyhemoglobin reaction of nitric oxide," Proc. Natl. Acad. Sci. USA (1999) 96:9027-9032.
Haga, Y. et al., "Biomedical microsystems for minimally invasive diagnosis and treatment," Proceedings of IEEE (2004) 92:98-114.
Herold, S. et al., "Mechanistic studies of S-nitrosothiol forimation by NO*/O2 and by NO*/methemoglobin," Arch. Biochem. Biophys. (2005) 436:386-396.
Hess, D.T, et al., "Protein s-introsylation: purview and parameters," Nat. Rev. Mol. Cell Biol. (2005) 6:150-166.
Jia et al., "S-nitrosohaemoglobin: a dynamic activity of blood involved in vascular control," Nature (1996) 380:221-226.
Kadish, K.M. et al., editors, Applications: Past, Present and Future. The Porphyrin Handbook, Academic Press: San Diego, CA (1999) vol. 6, pp. 240-250 (cover and table of contents only).
Kirchner, C. et al., "Corrosion protection and long-term chemical functionalization of gallium arsenide in an aqueous environment," Adv. Funct. Mat. (2002) 12(4):266-276.
Kruszyna, R. et la., "Nitrite conversion to nitric oxide in red cells and its stabilization as a nitrosylated valency hybrid of hemoglobin," J. Pharm. Exp. Thera. (1987) 241:307-313.
Lantoine, F. et al., "Selective and sensitive electrochemical measurement of nitric-oxide in aqueous-solution—discussion and new results," J. Electroanal. Chem. (1995) 392:85-89.
Lu, H. et al., "High temperature hall effect sensors based on AlGaN/GaN heterojunctions," J. Appl. Phys. (2006) 99:114510-1-114510-4.
Luchsinger, B.P. et al., "Assessments of the chemistry and vasodilatory activity of nitrite with hemoglobin under physiologically relevant conditions," J. Inorg. Biochem. (2005) 99:912-921.
Luchsinger, B.P. et al., "Routes to S-nitrosohemogiohin formation with heme redox and preferential reactivity in the beta subunits," Proc. Natl. Acad. Sci. USA (2003) 100:-461-566.
McMahon, T.J. et al., "Extrapulmonary effects of inhaled nitrix oxide: role of reversible S-nitrosylation of erythrocytic hemoglobin," Proc. Am. Thorac. Soc. (2006) 3:153-160.
McMahon, T.J. et al., "Nitric oxide in the human respiratory cycle," Nat. Med. (2002) 8:711-717.
Moore, E.G. et al., "Cooperativity in the dissociation of nitric oxide from hemoglobin," J. Biol. Chem. (1976) 251:2788-2794.
Pearton, S.J. et al., "GaN-based diodes and transistors for chemical, gas, biological and pressure sensing," J. Phys. Condens. Matter (2004) 16:R961R994.
Potter, W., "Reduction of nitric oxide to nitrous oxide by cobalt porphyrins and corrins," Fuel Proces. Tech. (1994) 40:355-360.
Rovira, c. et al., "Equilibrium geometries and electronic structure of iron-porphyrin complexes: a density functional study," J. Phys. Chem. A. (1997) 101:8914-8925.
Sharma, V.S. et al., "Reaction of nitric oxide with heme proteins and model compounds of hemoglobin," Biochem. (1987) 26:3837-3843.

(56) References Cited

OTHER PUBLICATIONS

Sharma, V.S. et al., "The dissociation of NO from nitrosylhemoglobin," J. Biol. Chem. (1978) 253:6467-6472.

Ship, N.J. et al., "Rates of release of nitric oxide from HbSNO and internal electron transfer," Bioorg. Chem. (2003) 31:3-10.

Singel et al., "Chemical physiology of blood flow regulation by red blood cells," Annu. Rev. Physiol. (1997) 67:99-145.

Smith, R.P., "Chemicals reacting with various forms of hemoglobin: biological significance, mechanisms, and determination," J. For. Sci. (1991) 36:662-672.

Stamler et al., Blood flow regulation by S-nitrosohemoglobin in the physiological oxygen gradient, Science (1997) 276:2034-2037.

Steinhoff, G. et al., "pH response for GaN surfaces and its application for pH-sensitive field-effect transistors," Appl. Phys. Lett. (2003) 83(1):177-179.

Stutzmann, M. et al., "CaN-based heterostructures for sensor applications," Dia. Related Matt. (2002) 11:886-891.

Taketa, F. et al., "Chain nonequivalence in binding of nitric oxide to hemoglobin," J. Biol. Chem. (1978) 253:5448-5451.

Talazac, L. et al., "Air quality evaluation by monolithic InP-based resistive sensors," Sensors and Actuators B: Chemical (2001) 76:258-264.

Talazac, L. et al., "Gas esnsing properties of pseudo-Schottky diodes on p-type indium phosphide substrates application to O3 and NO2 monitoring in urban ambient air," Sensors and Actuators B: Chenical (2002); 83:149-159.

Tsui, D.C., "Electron-tunneling studies of a quantized surface accumulation layer," Phys. Rev. B. (1971) 4(12):4438-4449.

Uhlrich, J. et al., "Interfacial chemistry and energy band line-up of pentacene with the GaN (0001) surface," J. Crys. Grow. (2007) 300:204-211.

Viktorovitch, P. et al., "Electronic Properties of InAs Surface Quantum Wells Grown on InP(100)," Second International Conference, Denver, Colorado (Apr. 23-25, 1990) 148-152.

Vilan, A. et al., "How organic molecules can control electronic devices," Trends in Biotech. (2002) 20:22-29.

Wierzbowska, K. et al., "Studies of gas sensing, electrical and chemical properties of n-Inp epitaxial surfaces," Physica Status Solidi(a) (2005) 203(9):2281-2286.

Wolter, S.D. et al., "Porphyrination of III-V compound semiconductor surfaces for detection of exhaled breath indicators of physiological status," Keynote lecture at SMCBS' 2007 International Workshop, See online Journal of SMCBS' 2007 International Workshop, 2 pages.

Zhao, Y. et al., "Thionitroxides, RSNHO: the structure of the SNO moiety in 'S-nitrosohemoglobin' a possible NO reservoir and transporter," J. Am. Chem. Soc. (2006).

United States Patent Office Action for U.S. Appl. No. 12/948,946 dated Feb. 1, 2012 (7 pages).

United States Patent Office Action for U.S. Appl. No. 13/201,181 dated Sep. 11, 2013 (20 pages).

United States Patent Office Final Action for U.S. Appl. No. 13/201,181 dated Jun. 16, 2016 (9 pages).

United States Patent Office Action for U.S. Appl. No. 13/201,181 dated Oct. 26, 2015 (9 pages).

Interntional Search Report and Written Opinion for Application No. PCT/US2015/020406 dated Jan. 14, 2016 (8 pages).

Garcia et al., Impact of Porphyrin Functional Groups on inAs Gas Sensors, Nov. 5, 2007.

Wu et al., Direct Detection of Low-Concentration NO in Physiological Solutions by a New GaAs-Based Sensor, Chemistry—A European Journal, vol. 7, Issue 8, Mar. 23, 2001, pp. 1743-1749.

International Search Report from PCT/US2009/047546, dated Nov. 2, 2009 (4 pages).

Written Opinion from PCT/US2009/047546, dated Nov. 2, 2009 (6 pages).

United States Patent Office Action for U.S. Appl. No. 13/201,181 dated Jan. 9, 2017 (13 pages).

United States Patent Office Action for U.S. Appl. No. 13/201,181 dated May 26, 2017 (4 pages).

\* cited by examiner

CHEMICAL SENSORS AND METHODS FOR MAKING AND USING THE SAME

CROSS-REFERENCE TO RELATED APPLICATIONS

This application is a national stage filing under 35 U.S.C. 371 of International Application No. PCT/US2009/047546, filed on Jun. 16, 2009, which claims the benefit of priority to U.S. Provisional Patent Application Ser. No. 61/129,273 filed Jun. 16, 2008, to U.S. Provisional Patent Application Ser. No. 61/129,274 filed Jun. 16, 2008, to U.S. Provisional Patent Application Ser. No. 61/136,072 filed Aug. 11, 2008, and to U.S. Provisional Patent Application Ser. No. 61/136,073 filed Aug. 11, 2008, each of which is incorporated herein by reference in its entirety.

FIELD OF INVENTION

The invention generally relates to chemical sensors comprising type III-V materials, and methods of making and using the same.

BACKGROUND

Chemical sensors are of great importance in health care, industrial processing, environmental monitoring and remediation, energy production, and national defense. The ideal chemical sensor would have one or more of the following characteristics: (1) fast response, (2) high sensitivity, (3) high selectivity, (4) capability of detecting and recognizing as many chemicals as possible, (5) low power consumption (e.g., not relying on ionization or vaporization) and (6) small, lightweight, compact, (7) easy to use, and (8) inexpensive. Achieving these characteristics, however, has been challenging in previous sensor applications, with no single sensor having all of these characteristics. While great strides have been made in sensor technology over recent years, many sensors are still too large, unreliable, and expensive for widespread and easy use. For example, mass spectrometry, which is both highly sensitive and highly selective, typically requires vacuum equipment, resulting in sensors which are not compact and have high power consumption. In contrast, inexpensive and easy to use sensors, such as in-home carbon-monoxide detectors, typically are limited to detecting only one or two chemical species.

SUMMARY

In one aspect, the invention may provide, among other things, a van der Pauw (VDP) sensor comprising an electronic circuit electrically coupled to a surface, the surface comprising a type III-V material, and the electronic circuit measuring a sheet resistivity of the surface using a VDP technique. The VDP sensor may further comprise a macromolecule, such as a porphyrin, an oligonucleotide, a protein, a polymer or a combination thereof in contact with the surface. The VDP sensors may be arranged in an array of similar or different sensors.

In another aspect, the invention may provide, among other things, a chemical sensor comprising an electronic circuit electrically coupled to a type III-V material having a two-dimensional electron gas, the electronic circuit measuring an electrical property of the type III-V material having a two-dimensional electron gas. The type III-V material may be in the shape of a surface or the type III-V material may form a portion of a heterostructure field-effect transistor (HFET) or a high-electron-mobility-transistor (HEMT). The sensor may further comprise a macromolecule, such as a porphyrin, an oligonucleotide, a protein, a polymer or a combination thereof in contact with the sensor. The sensors may be arranged in an array of similar or different sensors.

In another aspect, the invention may provide, among other things, a method of detecting a chemical comprising measuring a first sheet resistivity of a van der Pauw (VDP) sensor, contacting the sensor with an analyte that may or may not contain a chemical, and subsequently measuring a second sheet resistivity of the sensor, wherein a difference between the first and second sheet resistivities indicates the presence of the chemical. The method may further comprise the use of a VDP additionally comprising a macromolecule, such as a porphyrin, an oligonucleotide, a protein, a polymer or a combination thereof in contact with the surface. The method may further comprise the use of a VDP sensor array of similar or different sensors.

In another aspect, the invention may provide, among other things, a method of detecting a chemical, the method comprising measuring a first electrical property of a type III-V material having a two-dimensional electron gas, contacting the type III-V material with an analyte that may or may not contain a chemical, and subsequently measuring a second electrical property of the type III-V material, wherein a difference between the first and second electrical properties indicates the presence of the chemical. The type III-V material may be in the shape of a surface or the type III-V material may form a portion of a heterostructure field-effect transistor (HFET) or a high-electron-mobility-transistor (HEMT). The method may further comprise the use of a sensor additionally comprising a macromolecule, such as a porphyrin, an oligonucleotide, a protein, a polymer or a combination thereof in contact with the surface. The method may further comprise the use of a sensor array of similar or different sensors.

In another aspect, the invention may provide, among other things, a method of diagnosing a subject with a medical condition, the method comprising contacting a van der Pauw (VDP) sensor with a control sample and determining a baseline sensor response, contacting the VDP sensor with an exhaled breath sample of the subject and determining a subject sensor response, and comparing the subject sensor response to the baseline sensor response, wherein a difference between the subject sensor response and the baseline sensor response indicates a medical condition. The method may be used for the detection of medical conditions such as respiratory diseases, metabolic diseases, or digestive disorders.

In another aspect, the invention may provide, among other things, a method of diagnosing a subject with a medical condition, the method comprising: contacting a type III-V material having a two-dimensional electron gas with a control sample and determining a baseline sensor response, contacting the type III-V material having a two-dimensional electron gas with an exhaled breath sample of the subject and determining a subject sensor response, and comparing the subject sensor response to the baseline sensor response, wherein a difference between the subject sensor response and the baseline sensor response indicates a medical condition. The type III-V material may be in the shape of a surface or the type III-V material may form a portion of a heterostructure field-effect transistor (HFET) or a high-electron-mobility-transistor (HEMT). The method may be used for the detection of medical conditions such as respiratory diseases, metabolic diseases, or digestive disorders.

In another aspect, the invention may provide, among other things, a method of making a sensor, the method comprising functionalizing a surface comprising at least one of InAs, InN and a combination thereof with a macromolecule and coupling a circuit capable of measuring an electrical property of the surface.

In another aspect, the invention may provide, among other things, a sensor for detecting one or more chemicals in a fluid whereby the device comprises a) n-InAs or n-InN and intermediate ternary or higher order materials that possess comparable surface electronic properties, b) surface electronic properties that consist of a surface electron accumulation layer that couples to the charge state of bare and chemically modified surfaces, c) a porphyrin layer comprising a plurality of porphyrin molecules attached to said surface electron accumulation layer.

In another aspect, the invention may provide, among other things, an NO-species sensor for detecting NO-species in a fluid comprising a semiconductor structure comprising a) a VDP sensor for contacting said fluid, wherein said VDP sensor is a sheet VDP sensor that exhibits a difference in resistivity in the presence or absence of a NO-species, and b) at least four ohmic contacts evenly spaced along the periphery of said VDP sensor.

In another aspect, the invention may provide, among other things, a NO-species sensor for detecting NO-species in a fluid comprising a semiconductor structure comprising a) an InAs layer, and b) a metalloporphyrin layer comprising a plurality of metalloporphyrin molecules attached to said InAs layer.

Other aspects of the invention will become apparent by consideration of the detailed description and accompanying drawings.

BRIEF DESCRIPTION OF THE DRAWINGS

FIG. 13 B shows a paired measurement of two embodiments of a van der Pauw sensor comprising an InAs surface functionalized with hemin.

DETAILED DESCRIPTION

Figure 1A:
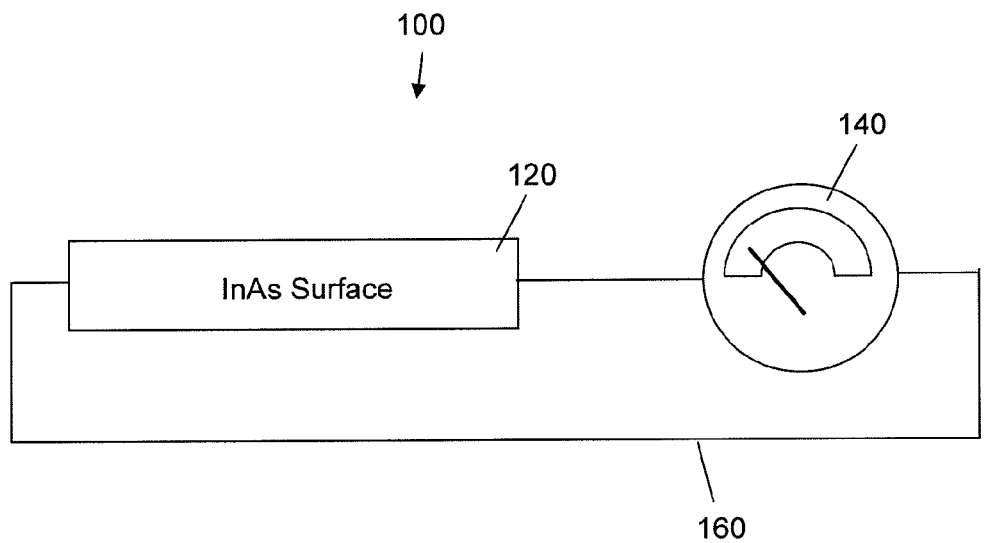
FIG. 1A is a general depiction of an InAs surface sensor.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Before any embodiments of the invention are described in detail, it is to be understood that the invention is not limited in its application to the details of construction and the arrangement of components set forth in the following description. The invention is capable of other embodiments and of being practiced or of being carried out in various ways. Also it is to be understood that the phraseology and terminology used herein is for the purpose of description and should not be regarded as limiting. The use of "including," "comprising," or "having" and variations thereof herein is meant to encompass the items listed thereafter and equivalents thereof, as well as additional items. Unless specified or limited otherwise, the terms "mounted," "connected," "supported," and "coupled" and variations thereof encompass both direct and indirect mountings, connections, supports, and couplings. Further, "connected" and "coupled" are not restricted to physical or mechanical connections or couplings.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

Further, no admission is made that any reference, including any patent or patent document, cited in this specification constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinency of any of the documents cited herein.

The invention generally relates to chemical sensors comprising type III-V materials. The sensors may comprise a surface comprising a type III-V material (in whole or part), supported by a substrate, and connected to a circuit capable of measuring electrical properties of the sensor. Type III-V materials are so named because they are mixtures of elements from columns III (B, Al, Ga, IN, Tl) and V (N, P, As, Sb, Bi) of the periodic table of the elements. By changing the ratio of the type III material to the type V material, it is possible to engineer a variety of band gap materials, thereby allowing for the construction of devices with desired properties. Examples of type III-V material include, but are not limited to, at least one of InAs, InN, GaN, GaAs, AlN, AlGaN, InAsN, InGaAs, and combinations thereof. In some embodiments, however, the type III-V material may exclude GaN. Examples of the electrical properties may include, but are not limited to, at least one of resistivity, conductivity, inductance, impedance, capacitance and combinations thereof.

Under the proper conditions, type III-V materials possess a two-dimensional electron gas (2DEG). The concept of a 2 dimensional electron gas (2DEG) is used to broadly describe electronic structures that are characterized as having a "sea" of electrons that are free to move in two dimensions, but are confined in the third. Such systems are known in semiconductor systems, and have been the basis for breakthroughs in semiconductor physics, such as the quantized Hall effect. Examples of type III-V materials possessing a 2DEG include, but are not limited to, InAs and InN, AlGaN/GaN heterostructures, and AlGaAs/GaAs heterostructures. For example, InAs and InN-based compound semiconductors and their derivative forms, such as ternary and quaternary compounds, exhibit conduction band bending below the Fermi level resulting in a surface accumulation layer of electrons, e.g., a 2DEG. The high concentration of electrons is believed to be a result of the pinning of the Fermi energy in the conduction band. In some senses InAs and InN are unique in that these materials possess highly conducting electrons confined to the near surface region. Accordingly, modifications in surface charge state, such as upon analyte capture by tethered functional groups or upon surface adsorption, leads to corresponding changes in carrier density in the near-surface and a measurable electronic signal. This property may be exploited to create sensors comprising type III-IV material having a 2DEG (e.g., InAs and InN) that are both highly responsive and sensitive to physabsorption or chemisorption of specific analyte molecules, i.e., useful chemical detection materials.

Some type III-V materials have 2DEGs at the surface of the materials (e.g., InAs, InN), while others have a 2DEG at an interface between type III-V materials in the presence of an appropriate electrical bias (e.g., GaN interfaced with AlGaN in a heterojunction field effect transistor (HFET) structure). The 2DEG makes these materials extremely sensitive to adsorbed chemicals which change the electrical properties of the 2DEG. Nonetheless, the sensitivity of 2DEG materials to adsorbed chemicals has not been fully appreciated nor used to create chemical sensors.

The sensors may include surfaces comprising type III-V materials, the surface of which has been functionalized with a macromolecule, such as at least one of a porphyrin, an oligonucleotide, a peptide, a polypeptide, a protein, a polymer and a combination thereof. Examples of porphyrins include, but art not limited to, at least one of tetraphenyl porphyrins, a hemin, a corrin, a chlorin, a corphin, and a combination thereof. Porphyrins are known to exist with (metalloporphyrins) and without central metal atoms, and both species may be functionalized to sensors of the invention. Metalloporphyrins may include, but are not limited to, iron porphyrins (FePP), nickel porphyrins (NiPP), copper porphyrins (CuPP), zinc porphyrins (ZnPP), and manganese porphyrins (MnPP). Iron containing porphyrins may be interchangeable referred to as hemins. Metal centers may include, but need not be limited to, Fe, Co, Ni, Zn, Mg, Mn, Cu, Ru, V, Pb, and Cr. Examples of oligonucleotides include, but are not limited to, polymers of nucleic acids, such as nucleic acids containing the bases cytosine, guanine, adenine, thymine, and uracil. Examples of peptides include, but are not limited to, polymers of amino acids. Examples of proteins include antibodies, ligands, hormones, cytokines, growth factors, receptors, receptor ligands. Examples of polymers may include, but need not be limited to, homopolymers, co-polymers, and block co-polymers comprising known monomer units, such as ethylenes, styrenes, vinyl chlorides, acrylics, urethanes, methacrylates, isobutalenes, haloethylenes, and lactones.

The sensors may be formed as van der Pauw (VDP) structures as set forth in more detail below, although they need not be van der Pauw structures. Van der Pauw (VDP) structures have primarily been used as Hall effect devices. The majority of Hall effect devices are galvanomagnetic sensors, magnetoresistors, semiconductor characterization devices, and other Hall plate magnetic sensors. While only a component of a Hall effect device, a VDP structure may exist in a much more simplified platform, not requiring an externally-applied magnetic field. Such sensors are simple, robust, and easily mass-produced. Although Hall devices have found a market niche for magnetic field sensing applications, VDP devices have not yet been exploited for molecular sensor applications.

Additionally, the sensors may be configured in arrays in order to make multiple simultaneous measurements with varied sensors. The sensors are capable of detecting a wide variety of chemicals contained in various fluids (air, water, blood, waste effluent, saliva, urine, etc.). Such sensors have applications in chemical and biological weapons sensing, explosives screening and detection, medical diagnostics, emissions control, combustion diagnostics, and environmental monitoring, among other applications.

Figure 1B:
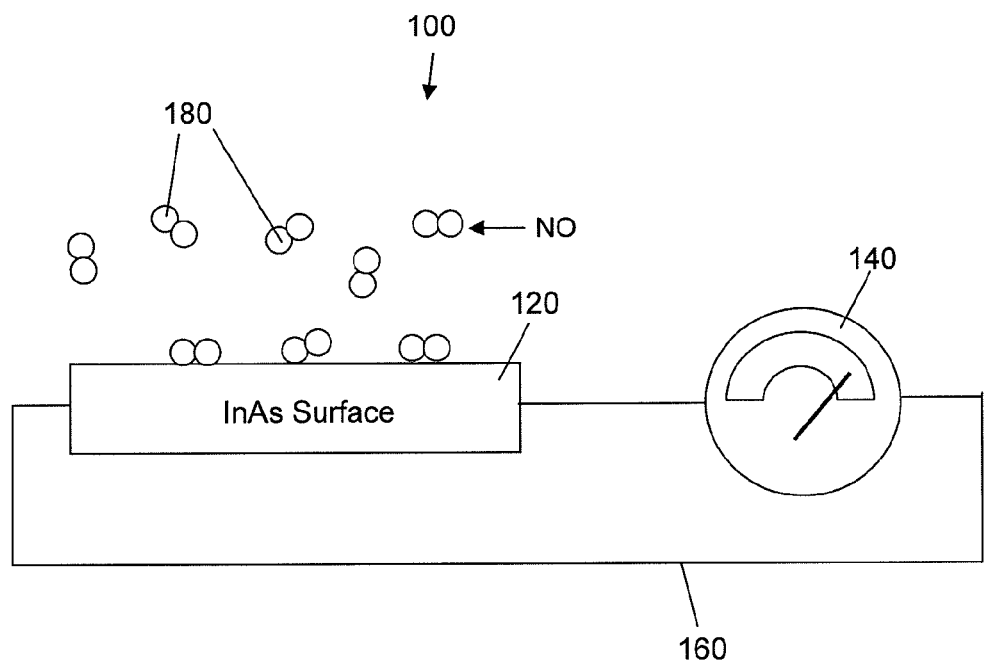
FIG. 1B is a general depiction of an InAs surface sensor in the presence of a chemical species, e.g., NO.

In one embodiment, a chemical sensor of the invention comprises a type III-V material, and in some instances, a type IIII-V material having a 2DEG, coupled to an electronic circuit capable of measuring an electrical property of the material. In the presence of an adsorbed species that causes a change in one or more of the electrical properties recited above of the 2DEG, the circuit will measure a change in the electrical property. This concept is illustrated by the embodiment shown in FIG. 1, showing InAs as one example of a type III-V material having a 2DEG. In FIG. 1A, InAs surface 120 is connected to electronic circuit 140 via electrical connections 160. In the absence of an adsorbed species that causes a change in the electrical properties of the type III-V material, electronic circuit 140 measures a first value of the electrical property. As shown in FIG. 1B, when nitric oxide (NO) 180 is introduced to chemical sensor 100, electronic circuit 140 measures a second value of the electrical property. Thus chemical sensor 100 allows for the detection of a chemical species by monitoring for a change in electronic circuit 140.

Electronic circuit 140 may measure any of a number of electrical properties of chemical sensor 100. For example, the resistivity of chemical sensor 100 may be measured by attaching four contacts to InAs surface 120 and monitoring the electrical potential between two contacts as a steady current is fed between the remaining two contacts. Other methods of measuring resistivity (or conductance) are known to those of ordinary skill in the art.

The capacitance of chemical sensor 100 may likewise be measured by attaching an electrode to opposite sides of InAs surface 120 and then monitoring for changes in the capacitance with a capacitance meter. Other methods for monitoring for changes in capacitance, such as the observation of the decay of an RC circuit, with InAs surface 120 acting as the capacitor, are known to those of skill in the art.

The inductance of chemical sensor 100 may also be measured by attaching an electrode to opposite sides of InAs surface 120 and then monitoring for changes in the inductance with an inductance meter. Other methods for monitoring for changes in inductance, such as the observation of the decay of an LC circuit, with InAs surface 120 acting as the inductor, are known to those of skill in the art.

A suitable electronic circuit 140 for the measurement of an electrical property of InAs surface 120 may be purchased from a number of known suppliers, such as Agilent (Palo Alto, Calif.), Tektronix (Richardson, Tex.), or Fluke (Everett, Wash.). Additionally, electronic circuit 140 can be constructed using card edge test equipment and software, such as that sold by National Instruments (Austin, Tex.). Multiplexed measurements, such as those necessary for evaluating arrays of sensors (discussed below), may require a specialized electronic circuit, however such methods are within the purview of the artisan of ordinary skill.

Figure 2:
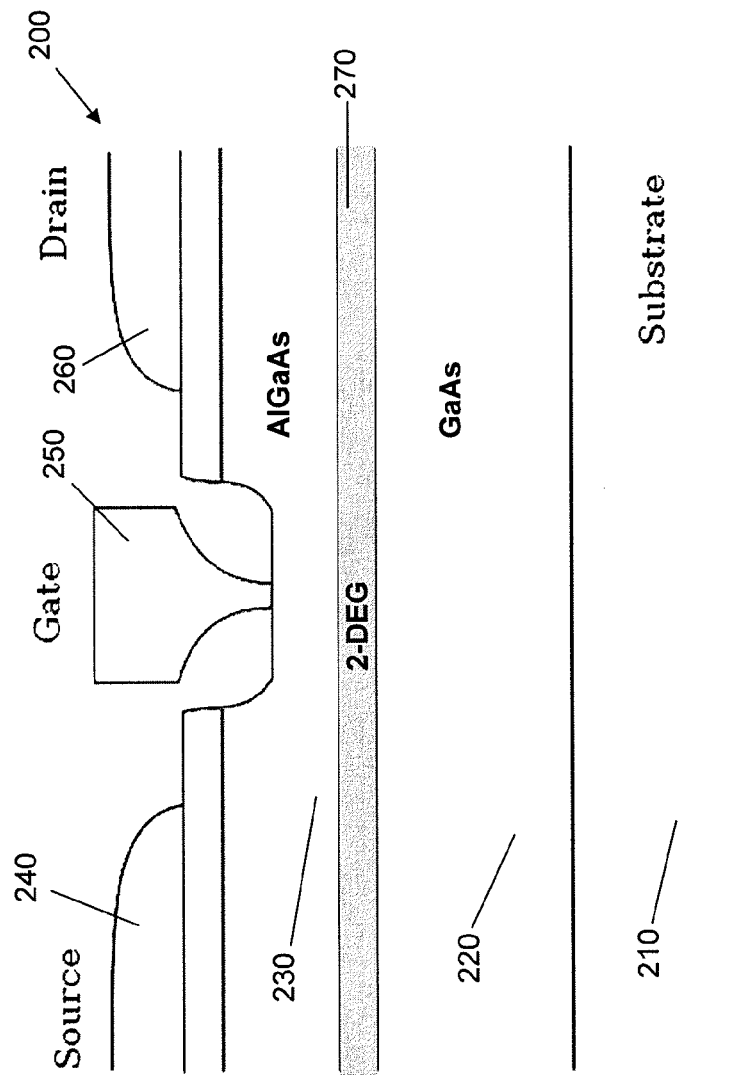
FIG. 2 is a general depiction of an AlGaAs/GaAs heterojunction field effect transistor (HFET).

The same 2DEG properties discussed with respect to chemical sensor 100 also make heterojunction structures suitable for use as chemical sensors. Heterojunction structure devices, such as heterostructure field-effect transistors (HFET) and high-electron-mobility-transistors (HEMT) are known in semiconductor physics, but the "buried" 2DEG has not been used as a chemical sensor. A standard HFET 200, comprising an AlGaAs/GaAs heterojunction is shown in FIG. 2. Standard HFET 200 comprises substrate 210 upon which is deposited GaAs layer 220, and AlGaAs layer 230, and the remaining structures of the transistor, namely source 240, gate 250, and drain 260 are fabricated thereon using known fabrication techniques. With this arrangement, 2DEG 270 is generated at the junction of AlGaAs layer 230 (a highly-doped wide-bandgap n-type donor-supply layer) and GaAs layer 220 (a non-doped narrow-bandgap channel layer). While Standard HFET 200 may be connected to an electronic circuit that is capable of measuring an electrical property (typically a voltage at a given bias), in most cases it is unnecessary to include source 240, gate 250, and drain 260 to produce a working sensor. Rather a heterolayer, such as AlGaAs/GaAs, can be deposited on a substrate and connected to an electronic circuit capable of measuring an electrical property of the material, similar to the structure shown in FIG. 1. The thickness of the components of the heterolayer will influence the size of the "buried" 2DEG, and also affect the sensor's response to adsorbed chemical species. The heterolayers are thinner than about 1 mm, typically thinner than about 100 µm, more typically thinner than about 10 µm. Heterojunction structures known to produce "buried" 2DEGs and suitable for use in the invention include, but are not limited to AlGaAs/GaAs, AlN/AlGaN, InAsN/IN, and InAs/InGaAs structures.

Figure 3A:
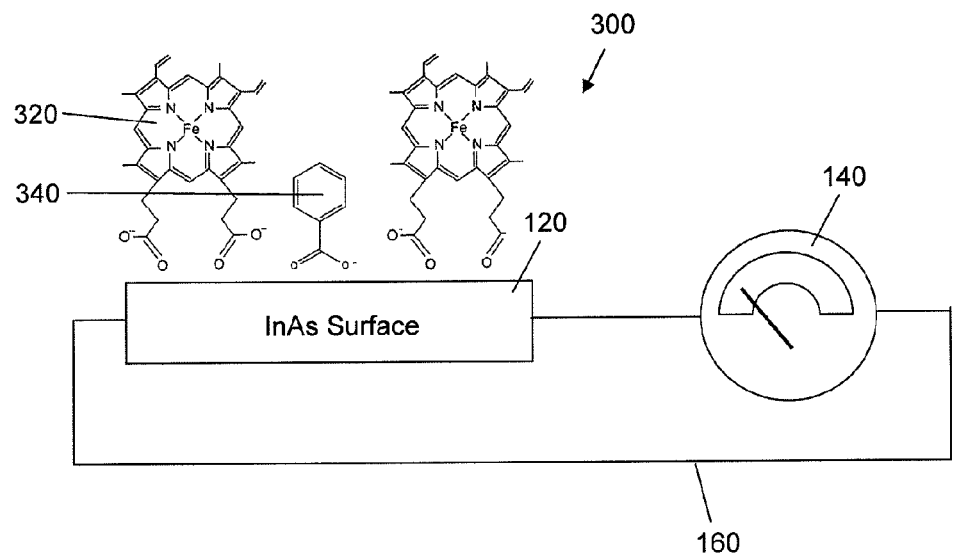
FIG. 3A is a general depiction of an InAs surface sensor functionalized with and Fe-hemin and benzoic acid spacers.
Figure 3B:
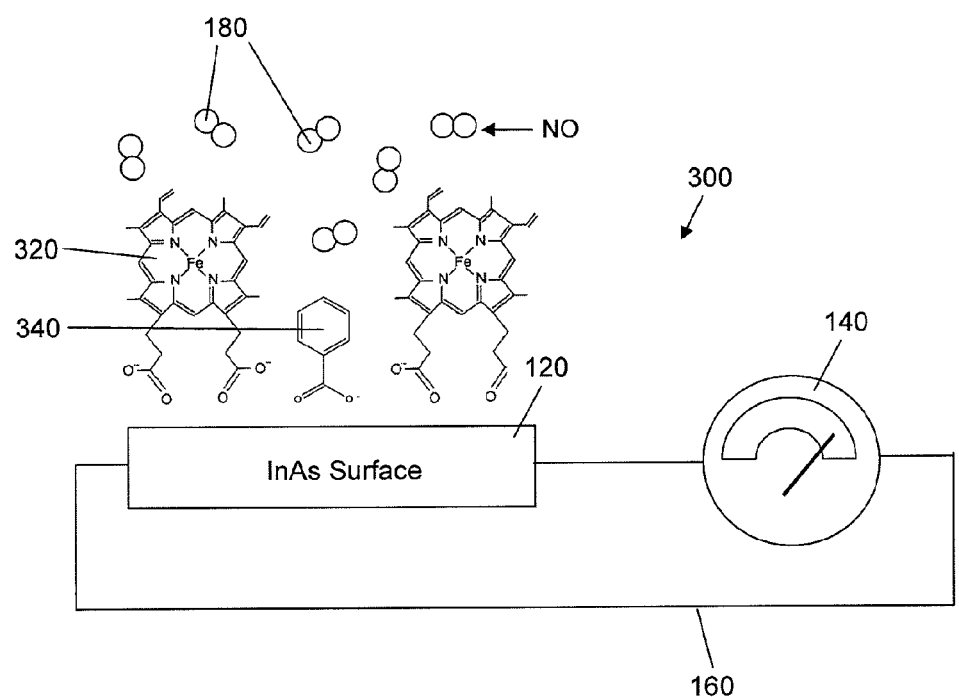
FIG. 3B is a general depiction of an InAs surface sensor functionalized with and Fe-hemin and benzoic acid spacers in the presence of a chemical species, e.g., NO.

While the 2DEG devices are sensitive to adsorbed species, the specificity of the sensors is dramatically increased with the functionalization of the 2DEG devices with macromolecules. The principle is illustrated in FIGS. 3A and 3B. Starting with a bare surface sensor, such as the InAs chemical sensor 100 shown in FIG. 1, it is possible to contact the 2DEG material with a macromolecule to produce functionalized chemical sensor 300, as shown in FIG. 3A. Functionalized chemical sensor 300 includes InAs surface 120, electronic circuit 140, and electrical connections 160. However, InAs surface 120 is contacted with hemin 320 and spacer molecules 340. In the absence of a chemical species that binds to hemin 320, electronic circuit 140 measures a first value of the electrical property. As shown in FIG. 3B, when nitric oxide (NO) 180 is introduced to functionalized chemical sensor 300, NO 180 binds to hemin 320, causing electronic circuit 140 to measure a second value of the electrical property. Thus functionalized chemical sensor 300 also allows for the detection of a chemical species by monitoring for a change in electronic circuit 140. By substituting hemin 320 for another macromolecule, such as a copper porphyrin, the sensitivity of functionalized chemical sensor 300 can be dramatically altered. Additionally, as is discussed below, it is possible to create arrays of multiple functionalized chemical sensors 300 to simultaneously detect mixtures of chemical species or to develop unique "fingerprint" signatures for particular chemical species.

As described above, one aspect of the invention is directed to exploiting the van der Pauw (VDP) resistivity measurement technique, typically used to determine various electronic material properties in the presence of a magnetic field, to measure changes in chemical concentrations of the target environment being sensed by the VDP sensors. The measurement of changes in chemical concentrations from the environment occurs when an electronic material's surface is sensitive and selective to a particular analyte and the adsorption of the analyte changes the conductivity of the sample through changes in the electronic state of the surface—which can be measured by the VDP technique of the invention. This methodology is significantly different and provides a number of advantages over current chemical sensors. One significant advantage is the enhanced accuracy of the four point probe averaging technique of the VDP sensor which reduces the effects of the resistance of individual contacts. Another advantage is the lack of need for a reference electrode since there is no "gate" potential applied, such as used in ISFETs (ion-sensitive field effect transistor). Finally, the uniformity of the field lines due to the symmetry of the van der Pauw structure could provide more sensitivity to surface charge changes in the active area in addition to field enhanced chemical adsorbtion/desorption processes.

Figure 4:
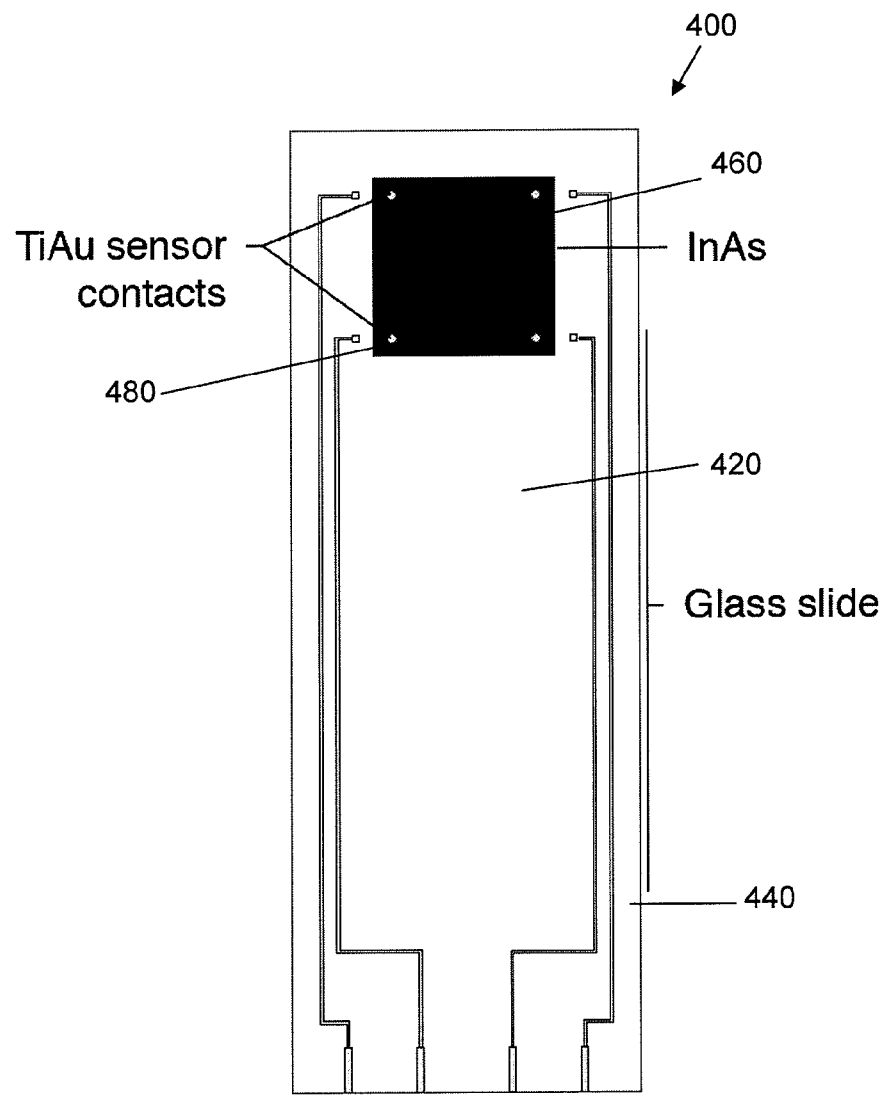
FIG. 4 shows an embodiment of a van der Pauw sensor of the invention.

An embodiment of a VDP sensor 400 is shown in FIG. 4. VDP sensor 400 comprises glass slide 420, upon which electrical contacts 440 have been printed. InAs surface 460 is contacted to glass slide 420. TiAs ohmic contacts 480 are then deposited onto InAs surface 460, and then electrical contacts 440 are connected to TiAs ohmic contacts 480 using gold wires (not shown). The completed VDP sensor 400 is then interfaced to an electronic circuit (not shown) capable of measuring the surface resistivity of InAs surface 460 using the van der Pauw technique (discussed below). As illustrated in FIG. 1, the electronic circuit measures a different surface resistivity based upon the presence of adsorbed species.

In some sensors using van der Pauw configurations, a current is applied across a first edge of the type III-V semiconductor material and the voltage is measured at a second edge on the opposite side of the sample. Typically the process is then repeated with a different set of edges and applied current direction. For example, a current can be applied across the second edge (or another edge) while a voltage measurement is made on a different (e.g., the first) edge. The resulting voltage measurements may be used to determine the sheet resistivity of the type III-V semiconductor material or the type III-V semiconductor material functionalized with antibodies. As is known in the art, a square van der Pauw sensor has two sets of opposing edges and measurements may be taken from both sets of edges. The results of the multiple measurements may be averaged to yield a value for the sheet resistivity of the type III-V semiconductor material or the type III-V semiconductor material functionalized with antibodies.

In another embodiment, a square piece of type III-V semiconductor film is secured on a glass slide with metallized contacts, as shown in FIG. 4. Semiconductor films are available from a number of suppliers including IQE, Inc. (Bethlehem, Pa.). The metallized contacts may be connected to the type III-V film with gold wires, for example. The type III-V film may also be connected to exterior circuitry with push pins and probe cards designed to receive sensor films. Other methods for producing exterior connections to the type III-V film may be achieved with known techniques of lithography, e.g., ion beam lithography and photolithography.

Figure 5:
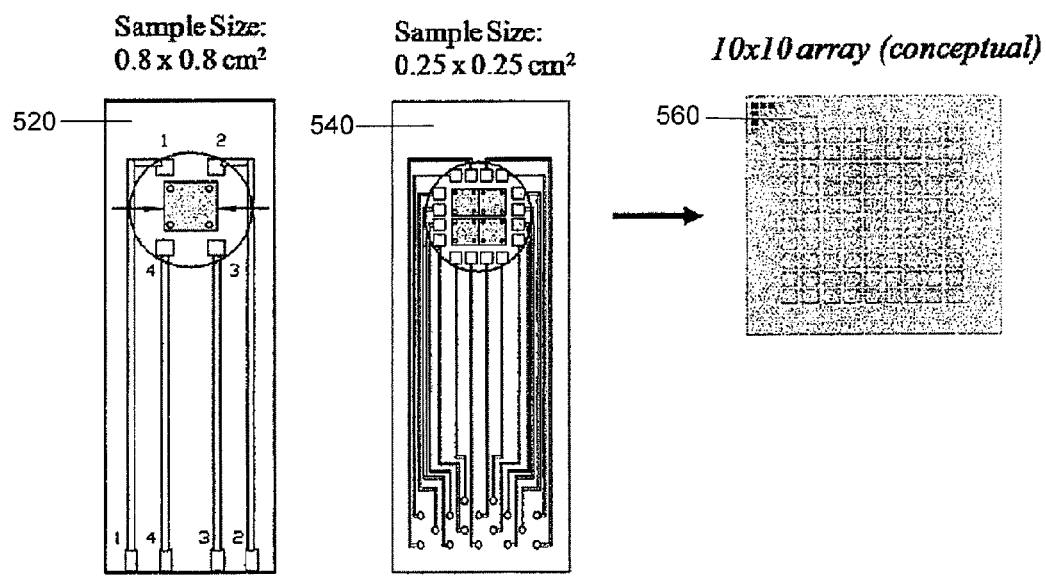
FIG. 5 shows embodiments of a single van der Pauw sensor, a 2×2 array of van der Pauw sensors, and a 10×10 array of van der Pauw sensors

The sensors of the invention may be scaled down so that hundreds, or thousands, of sensors can be fit on a substrate to make an array of sensors. This principle is illustrated in FIG. 5, which compares single VDP sensor 520, to 2×2 VDP sensor 540, to 10×10 VDP sensor 560. In principle, using known lithographic techniques and evaporative deposition, it may be possible to create even larger arrays of type III-V materials surfaces each with four contacts sufficiently insulated from each other to allow independent sheet resistivity measurements of each type III-V materials surfaces. Larger arrays of VDP sensors will allow for multiplexing measurements whereby simultaneous measurements of hundreds or thousands of sensors can be made. Because of the large number of sensors, it will be possible to include multiple functionalities among the sensors for wide sensitivity, as well as duplicate sensors to assure reliability. Furthermore, by constructing sensors with varying sensitivity to chemical species, it is possible to dramatically increase the dynamic range of the sensors.

Like the 2DEG sensors of FIGS. 1 and 2, VDP sensors, such as those shown in FIGS. 4 and 5, may be functionalized with macromolecules, as illustrated in FIG. 3. Properly functionalized, the macromolecules act as transducers modify the resistivity of the sensor upon analyte capture. Using functionalized VDP sensors allows the detection of chemical changes in fluid (gaseous or aqueous) environments as described below. Furthermore, VDP sensors of the invention can be fabricated into one-, two- or three-dimensional arrays of VDP sensors with each sensor optionally chemically functionalized (using porphyrin compounds) for broad analyte detection capability. The VDP sensors, arrays, and devices may be microfabricated into various geometries and dimensions; and supporting circuitry (for data measurement, processing, and analysis) can be fabricated onto the same semiconductor substrate for fabrication cost savings. Alternatively, the VDP structures (sensors, arrays and devices) may be fabricated into a plurality, such as two or more, semiconductor substrates and connected after fabrication. This highlights one of the important benefits of this sensor platform, the VDP sensors, devices and arrays of the invention is a relatively simple design which can be economically produced in high or low quantities.

The method of making functionalized sensors typically comprises constructing a VDP sensor, as outlined above and then functionalizing the surface with one or more macromolecules and a spacer. Typically the surface is degreased, wet etched, and then exposed to a solution comprising the macromolecules. The VDP sensor then sits for a period of time in contact with the solution comprising the macromolecules. The solution of macromolecules is removed, the VDP sensor is washed with an organic solvent and the VDP sensor is dried with dry nitrogen. The surface may be degreased with acetone, or other suitable organic solvents including, but not limited to ketones, mineral spirits, or naphthas. Type III-V semiconductor materials may be wet etched with hydrofluoric acid diluted in a solvent, including but not limited to, methanol, ethanol, and isopropanol. The prepared surfaces are exposed to the solutions comprising the macromolecules for greater than about 1 hour, typically greater than about six hours, more typically greater than about 12 hours. In some embodiments, it may be beneficial to gently agitate the prepared surfaces while the solution comprising the macromolecules is allowed to contact the prepared surfaces. A laboratory orbital shaker, or other similar device, may be used to agitate the prepared surfaces while they are contacted with the solution comprising the macromolecules. Organic solutions of macromolecules are prepared at concentrations less than 1M, typically less than 100 mM, more typically less than 10 mM. The solvent may be dimethylformamide (DMF), or another suitable organic solvent. The macromolecules may be intermixed with spacer molecules in a ratio of 10:1 to 1:10. Typically, the macromolecules and spacers are mixed in a ration of about 1:1. Spacer molecules are typically benzoic acid or derivatives of benzoic acid. Derivatives of benzoic acid include, but are not limited to, substituted benzoic acids, including esters, halides, amines, and amides of benzoic acid, such as para-amino benzoic acid. After contacting the surface for some time the macromolecule solutions are rinsed away with a dilute aqueous mixture of chlorinated solvents, such as 5% v/v chloroformalhexane, and the surface dried with inert gas (Ar, $N_2$, He, Ne, $SF_6$).

To produce arrays of functionalized sensors with different functionalities, a system of wells atop each sensor may be created to assure that the correct macromolecule is added to the correct sensor. Additionally, it may be possible to print the macromolecules on the appropriate sensors using known technology, such as ink-jet or screen printing. For example 10×10 VDP sensor 560 may require a 10×10 overlay of protective material that may be reversibly bonded to the sensor to create a 10×10 array of reservoirs suitable for degreasing and wet-etching the surfaces in preparation for receiving solutions comprising macromolecules. After the surfaces have been prepared, 100 different solutions comprising macromolecules can be distributed into the 100 separate wells using known microfluidic techniques. After an appropriate reaction time, the 100 wells may be aspirated, washed with solvents, and dried. The overlay can then be removed to yield a finished sensor. Such an array would be dramatically less expensive to operate than other chemical array sensors. It is also conceivable that such arrays may be incorporated into a handheld device to allow mobile detection of chemical species.

Another aspect of the invention is directed to a method of detecting a concentration of a molecular species (e.g., $NO_x$-species) in a fluid. It was found that the change in sheet resistivity in a VDP sensor is related to the concentration of a molecular species such as a NO-species, in a fluid. This relationship may be exploited to determine concentrations of any analyte in any fluid providing that the analyte affects a measurable resistivity change by the VDP sensor. Furthermore, signal processing means are known to manually or automatically translate the readings from the VDP sensors into actual concentrations. A few methods for determining concentrations are shown below with the understanding that the methods of this disclosure are not limited to these means.

One method of determining concentration compares the resistivity of a VDP sensor in contact with a fluid (gas or liquid) of known concentration and unknown concentration. If the resistivity is similar, the molecular species (e.g., $NO_x$-species) concentration of the fluids would also be similar. In one preferred embodiment, a VDP sensor may be calibrated with a number of fluids each with a known concentration of a molecular species (e.g., $NO_x$-species) covering the range of expected concentrations. A response curve may be drawn or stored electronically. A VDP sensor resistivity reading based on a measurement of an unknown sample may be compared to the response curve and the concentration of a molecular species (e.g., $NO_x$-species) in the unknown sample may be determined directly with or without interpolation, extrapolation, or modeling. Methods of interpolation and extrapolation, including linear and polynomial methods are known. In a preferred embodiment, only interpolation methods are used to determine concentration. An alternative method for determining concentration is to use one or more reference VDP sensors in contact with one or more fluids with known but different concentrations of a molecular species (e.g., $NO_x$-species). A reading from a VDP sensor testing an unknown fluid may be compared to the reading from reference VDP sensors and the concentration may be determined by interpolation or extrapolation. In either method for measuring concentration (using a reference curve) the values may take into account differences in temperature, pressure, and fluid composition.

Another aspect of the invention is directed to a method of identifying a molecular species (e.g., $NO_x$-species) in a fluid using a molecular species (e.g., $NO_x$-species) sensor comprising an array of VDP sensors. The method comprises the step of contacting two or more molecular species sensors to the fluid, wherein at least two of the two or more molecular species sensors is different. In a second step, two or more sheet resistivities from the two or more $NO_x$-species sensors is measured by a van der Pauw measurement method through the ohmic contacts of each sensor. Based on the sheet resistivities, the presence of the molecular species may be detected.

Sensors of the invention may useful for detecting a number of chemical species including, but not limited to, NO, $NO_2$, $O_2$, CO, $CO_2$, $SO_2$, $NH_3$, nitrates, nitrites, sulfates, sulfites, and volatile organic materials (VOCs). Such species include drugs, explosives, environmental pollutants, hormones, and toxins. Furthermore, the sensors of the invention can detect these chemical species in fluid analytes including air, water, blood, waste effluents, exhausts, saliva, tears, sweat, urine, and exhaled breath. Such flexibility will allow sensors of the invention will find use in health care, industrial processing, environmental monitoring, security screening, and national defense. Because the sensors can measure chemical concentrations in a variety of body fluids, the sensors will be useful for performing real-time assessment of pharma-kinetics for individual subjects, e.g., personalized medicine.

Furthermore because sensors of the invention are both sensitive and inexpensive to produce, the sensors will be useful for incorporation into disposable medical devices for the assessment and treatment of medical conditions. Such conditions include, but need not be limited to, respiratory diseases (emphysema, asthma, cystic fibrosis), metabolic diseases (cirrhosis, diabetes, phenylketononurea), cardiac diseases (ischemia, hypertension, congestive heart failure) and digestive disorders (ulcers, acid reflux). For example, a breath analyzer that is sensitive to parts-per-billion (ppb) levels of NO may allow for faster identification of respiratory diseases such as asthma. The sensors can also be used for health status monitoring of mammals, especially livestock, including cattle, swine, and poultry.

The below examples are not intended to limit the scope of the invention in any way, but are provided to illustrate the principles of the invention and to demonstrate the capabilities of the sensors of the invention.

EXAMPLES

Example 1—InAs van der Pauw (VDP) Sensor

A VDP sensor, similar to that shown in FIG. 4, was fabricated as follows: A 1 cm×1 cm square of InAs film (IQE, Inc.) was mounted with double sided tape (3M, St. Paul, Minn.) on a glass slide (Fisher Scientific, Waltham, Mass.) having electrical contacts bonded to the surface. (See, e.g., FIG. 4.) Gold wire (Surepure Chemetals, Florham Park, N.J.) was bonded between the electrical connections and the four corners of the InAs square with a solvent resistant epoxy (Resinlab EP1785, Resinlab, Germantown, Wis.). The resulting arrangement will allow for measurements of sheet resistivity of the InAs square using the van der Pauw method. The connections between the InAs square and the electrical connectors were confirmed with a voltmeter (Fluke, Everett, Wash.). After electrical continuity was verified, the sensor was cleaned with acetone and isopropyl alcohol, and then dried with $N_2$.

Example 2—InAs van der Pauw (VDP) Sensor

A second type of VDP sensor may be formed as follows: 40 nm of InAs was grown on a 1 cm×1 cm semi-insulating, Fe-doped InP substrate in a Riber 2300 molecular beam epitaxy (MBE) system. The buffer layer was grown to reduce lattice mismatch at the InAs/InP interface. There was no intentional doping and the measured sheet carrier Hall concentration for the InAs samples were about $4.0 \times 10^{12}$ $cm^{-2}$ and the Hall mobilities were $\sim$1980 $cm^2/Vs$.

In order to minimize the error for measurement of the material's electrical properties, four Ti/Au ohmic contacts are applied to the corners of the sample, (See FIG. 4). The contacts are then annealed in forming gas at 400° C. for 30 s. The arrangement of the contacts allows for the calculation of the bulk sheet resistivity ($R_{SH}$) by applying current and measuring voltage from opposite pairs of contacts. The bulk sheet resistivity measurements will be performed in 8 different measurement configurations to provide a measure of $R_{SH}$.

The VDP devices were attached to a printed circuit board and electronically connected with Au wire-bonds for sensor measurements. The surfaces of the samples were degreased with acetone and isopropyl alcohol and dried with $N_2$ gas before testing (see below).

Example 3—AlGaN/GaN Heterostructure Field Effect Transistor (HFET)

AlGaN/GaN heterostructures were also constructed to evaluate their performance as a chemical sensing platform. GaN-based devices are anticipated to offer great sensitivity as an active transduction platform. As discussed above, HFET (heterostructure field effect transistor) structures are generally characterized by a well-defined two-dimensional electron gas (2DEG) layer formed in the near region of two coincident, epitaxial semiconductors. The induced polarization at this interface for III-V heterojunctions leads to charge densities as high as $10^{13}$ cm$^{-2}$. An interesting consequence of the HFET design is the dependence of the 2DEG properties on the surface electronic or charge state. Because of this surface charge coupling III-V gateless HFET structures, including AlGaN/GaN, have been shown to be sensitive to the adsorption of molecules.

A AlGaN/GaN HFET structure similar to that shown in FIG. 2 was fabricated using known techniques and electrical connections were made using spring clips and insulated cabling. The spring clip connectors were connected to a Hall switching card (Keithley, Inc.) which switches connects (connecting to a current source, picoammeter, and voltmeter) with a serial data cable threaded through a rubber stopper.

Example 4—InAs van der Pauw (VDP) Sensor with Functionalized Hemin and Benzoic Acid Spacers The InAs VDP sensor of Example 2 is further functionalized with hemin as follows: After the sheet resistivity response of the InAs VDP sensor of Example 2 was verified as functional, the InAs surface was again degreased with brief ultrasonic scrubbing in solvents. A 1 mM hemin-Cl and benzoic acid (1:1) solution was prepared in dimethylformamide (DMF), and the InAs surface was allowed to contact this solution for approximately 1 hr. As described above, the benzoic acid acts as a surface spacer between hemin groups to prevent polymerization and promote upright orientation of the hemin (see FIG. 3). After contacting the hemin/benzoic acid solution was rinsed away with 5% v/v chloroformalhexane and the InAs surface was dried with Ar gas. Functionalized samples were subsequently loaded into the XPS system for surface chemical analysis.

XPS characterization was performed on the samples both before and after functionalization with the hemin and benzoic acid solution. For these samples the survey scan, C1s, O 1s, Fe 2p, In 3d, and As 3d core level spectra, and valence band regions were evaluated. A Kratos Axis Ultra™ XPS system was used with a monochromatic, Al Kα source (kinetic energy of 1486.6 eV and pass energy of 20 eV for core level and valence band regions) and the data was processed using CasaXPS™ software. Binding energy (BE) calibration for the XPS data was implemented by assigning the In $3d_{5/2}$ peak at 444.25 eV for In—As bonding. The valence band regions were primarily used to extrapolate the valence band maximum (VBM) values to observe how the surface bands change as a result of chemical functionalization. Following XPS characterization the resistivity response of the functionalized samples was measured during exposure to the four gases and compared to their response in the bare-surface state.

Example 5—Analysis of VDP Sensor Performance in Test Cell

Figure 6:
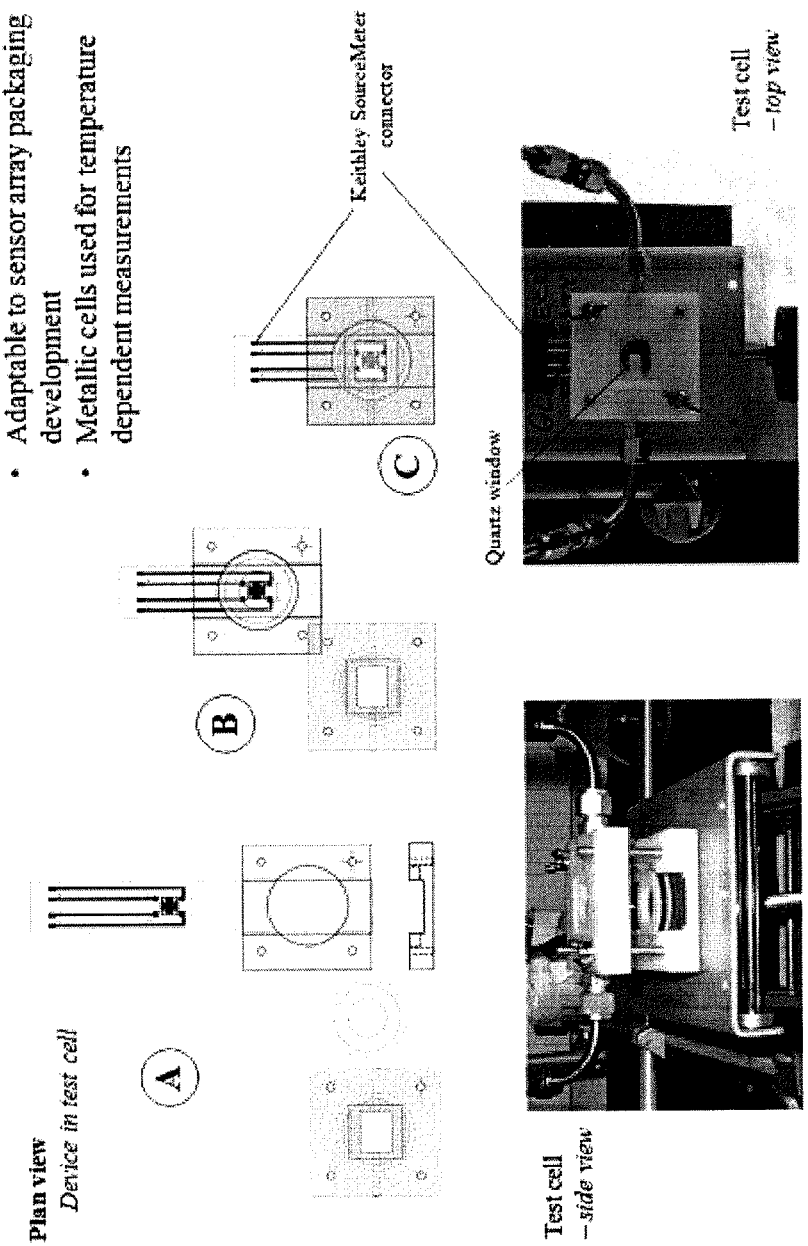
FIG. 6 shows a test cell that was used to test sensors of the invention.
Figure 7:
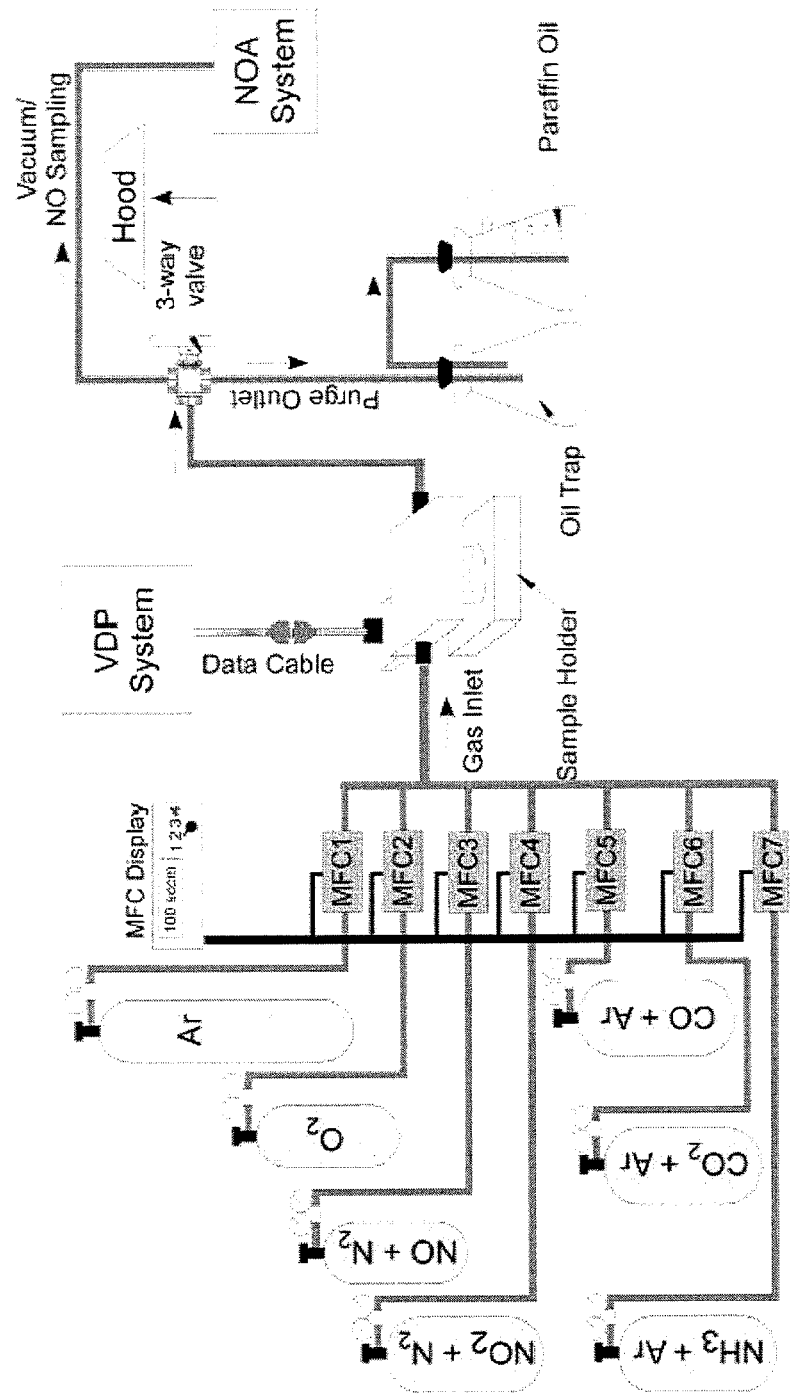
FIG. 7 shows an experimental setup that is used to measure the performance of sensors of the invention with a test cell similar to FIG. 6.

The performance of functionalized and unfunctionalized VDP and HFET sensors was evaluated with the test cell shown in FIG. 6, using the experimental setup shown in FIG. 7. A glass and Teflon experimental cell was sealed with viton gaskets and has two access ports; a gas mixture inlet and a gas purge outlet which maintains near atmospheric pressure conditions at room temperature (see FIG. 6). The gas mixture inlet was connected to four individual MKS, Inc. mass-flow controllers (MFCs) for Ar, NO (70 ppm) balanced in Ar gas, $NO_2$ (55 ppm), and pure $O_2$ (from National Welders), as shown in FIG. 7. A chemiluminescent SIEVERS™ NO Analyzer (NOA) was used to verify the 70 ppm NO concentration (see FIG. 7).

Example 6—Comparison of InAs VDP Sensors, InP VDP Sensors, and GaN HFET Sensitivity An InP VDP sensor was formed using the techniques of Example 2. Using the test cell and experimental setup described in Example 5, the sensitivities of an InAs VDP sensor (Example 2), the InP VDP sensor, and a GaN HFET (Example 3) were compared for static exposure to low concentrations of NO and $NO_2$ in a balance of Ar. The NO concentration levels were calibrated and captured in real-time by an independent Nitric Oxide Analyzer (NOA—from SIEVERS, Inc.) via a 3-way valve, which redirected gas flow to the NOA. The NOA was connected to a computer via a serial connection and a LabVIEW program was used to monitor and document experimental data.

Figure 8:
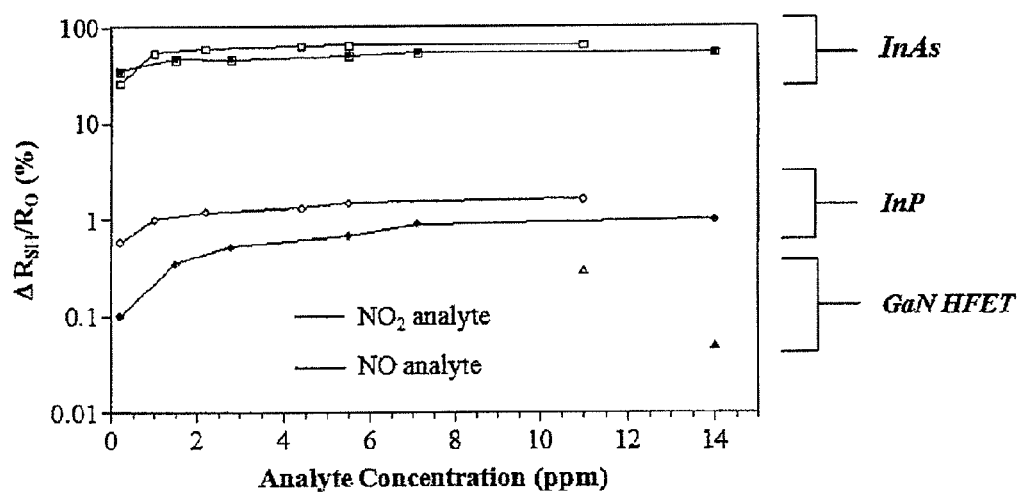
FIG. 8 compares sensitivities of InAs surface sensors, InP surface sensors, and GaN HFETs.

As is evident from FIG. 8, the InAs VDP sensor was more sensitive to both NO and $NO_2$ than the InP VDP sensor, and both VDP sensors were more sensitive to the NO and $NO_2$ than the GaN HFET. The y-axis, $\Delta R_{SH}/R_0$, is the normalized sheet resistivity response, used to reflect differences in nascent sheet resistivity among sensors of different construction.

The non-functionalized sheet resistivity changes with time in response to NO appear to follow a pattern that can be described by the Langmuir gas adsorption kinetics model shown in the equation:

$$N(t) = \frac{N^* P}{P + b}(1 - e^{\frac{t}{\tau}})$$

where N(t) is the concentration of gas species adsorbed at time t, N* is the concentration of adsorption sites, P is the gas pressure, b is the adsorption constant, and T is the time constant (or inverse of the adsorption rate constant). The primary response time windows for each data set were imported into Mathematica™ and the constants in equation 1 were solved by finding the least squares fit. A summary of the results of these Langmuir fits to the sheet resistivity response data and the approximate changes in sheet resistivity due to NO exposure ($\Delta R_{SH}$) indicated Time Constants of about 48 min. and Fit Errors of about 0.05%. (See inset, FIG. 9)

Example 7—Response of Unfunctionalized InAs VDP Sensor to Analyte Gasses

Figure 9:
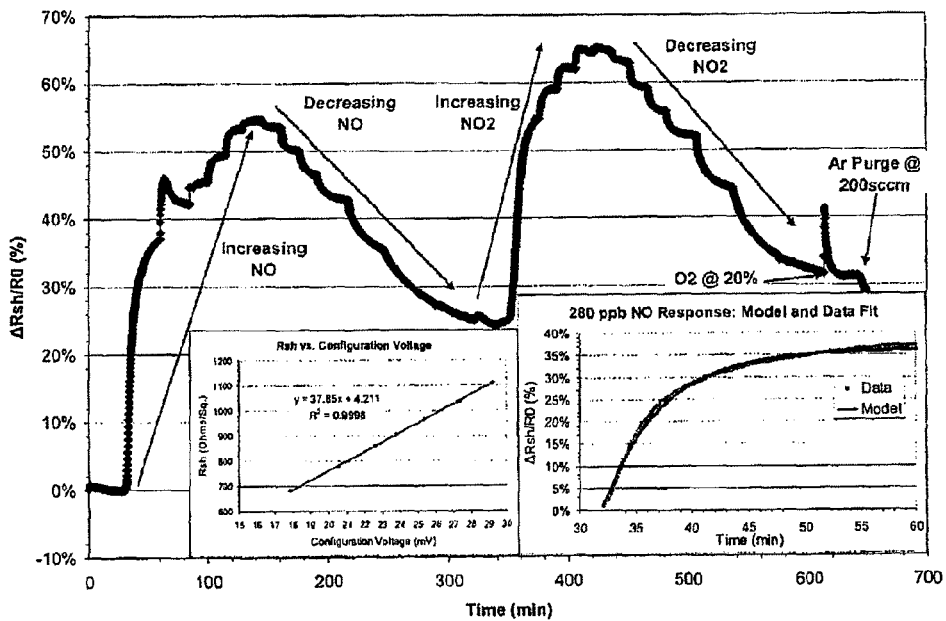
FIG. 9 shows the response of a van der Pauw sensor comprising an InAs surface without surface functionalization.

An InAs VDP sensor was formed using the techniques of Example 2. FIG. 9 shows the normalized sheet resistivity response (($R_{SH}-R_0$)/$R_0$, where $R_0$=675 Ω/sq.) of pre-functionalized InAs sensor to NO, $NO_2$, and $O_2$ at varying gas concentrations. For NO and $NO_2$ gases the relative flow ratios of the analyte gas to pure Ar were automated to change in scheduled steps (0.0%, 0.4%, 2%, 4%, 8%, 10%, and 20%) for fixed amounts of time while keeping the total flow constant at 500 seem. The analyte concentrations were then stepped back down until pure Ar was again purging the experimental cell at 500 seem. At the end of the experiment pure $O_2$ flow was set to 20% of the total flow to simulate dry air for 45 minutes. Finally, the cell was purged with pure Ar.

To decrease the time between measurements only one VDP configuration was measured (i.e. 200 µA sourced between contacts 1 and 2 and voltage measured between 3 and 4). During the gas response experiment the full sheet resistivity measurement was periodically taken (all 8 VDP configurations) and a linear relationship was plotted to calculate the sheet resistivity from the single-configuration measured voltages (as shown in the bottom-left inset of FIG. 9). This configuration allowed data to be collected every 2 seconds for the single-configuration voltage versus 180 seconds for the normal VDP method.

The resistivity responses of unfunctionalized InAs to NO and $NO_2$ generally follow an exponential rise with increasing analyte concentrations and slower decay with decreasing concentrations. These exponential behaviors are similar to Langmuir adsorption kinetics common in semiconductors with sensitive surface space-charge regions.

As illustrated in the bottom-right inset of FIG. 9, an exponential model ($R_{SH}=R_{start}+A \exp(-t/\tau)$) was used to extrapolate the time constant from the sample $R_{SH}$ response to each analyte concentration, where $\tau$ is the time constant and A is a fitting parameter (see Example 5).

Figure 10:
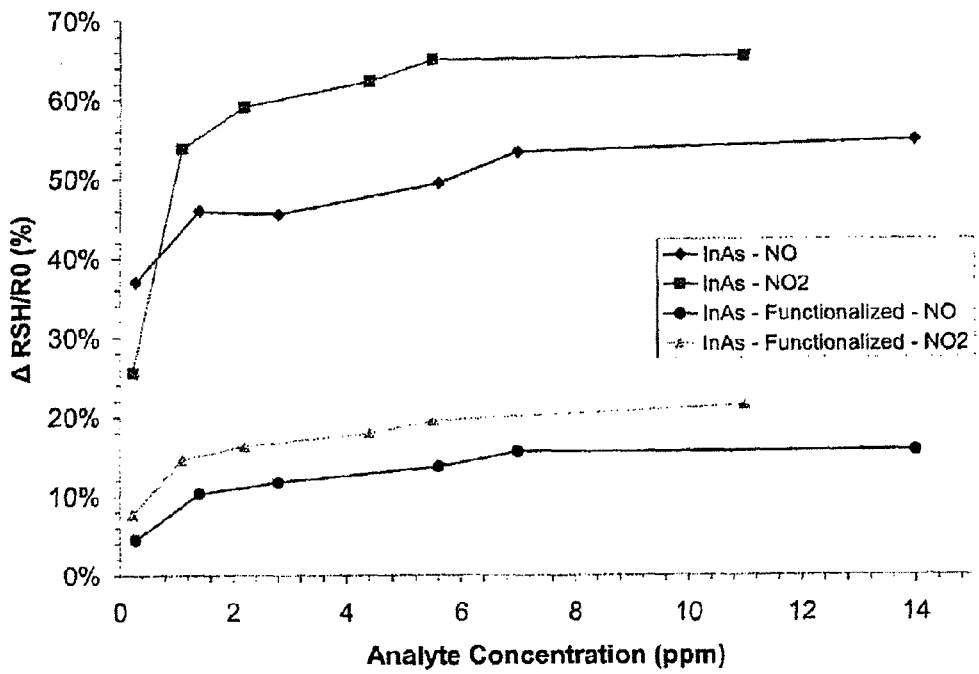
FIG. 10 compares the response to NO and $NO_2$ of functionalized and unfunctionalized InAs van der Pauw sensors.

Example 8—Comparison of Functionalized and Unfunctionalized InAs VDP Sensors to Analyte Gasses The responses of unfunctionalized InAs VDP sensors (Example 2) and hemin-functionalized VDP sensors (Example 4) are compared in FIG. 10. As evidenced by FIG. 10, the bare-surface InAs material system had significantly larger changes in resistivity in response to NO and $NO_2$ gases. Although the hemin functional group reduced the InAs conductivity sensitivity, the time constants for the responses were also reduced to under a minute. This fast time response would be particularly useful in explosives or hazardous chemical exposure detection applications.

Example 9—Response of Heme-Functionalized InAs VDP Sensor to Analyte Gasses

Figure 11:
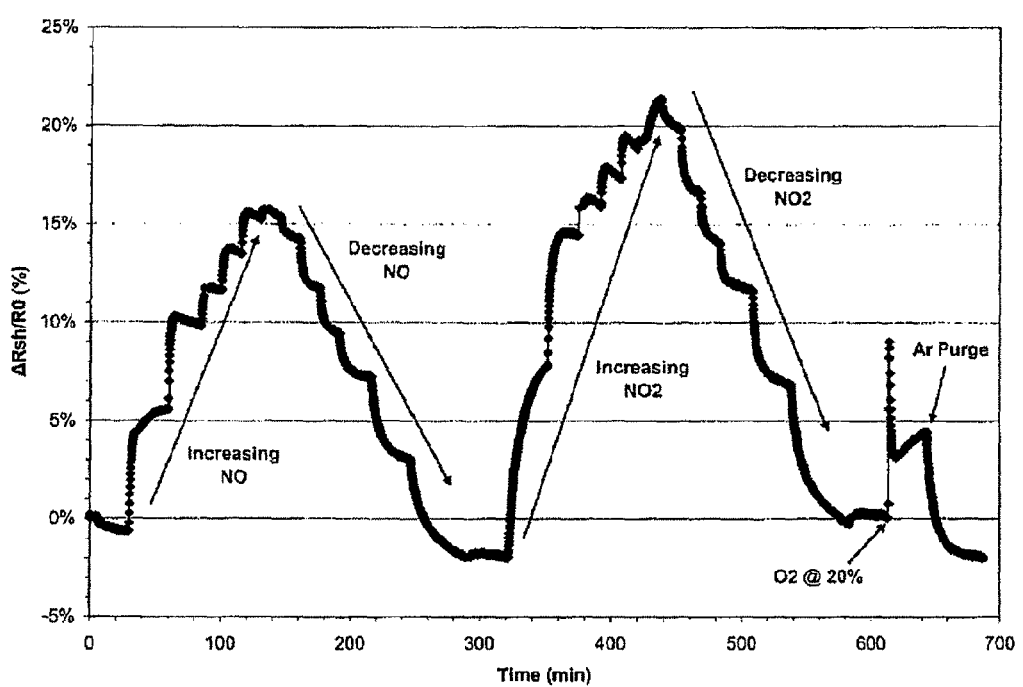
FIG. 11 shows the response of an embodiment of a van der Pauw sensor comprising an InAs surface functionalized with hemin and benzoic acid when exposed to NO and $NO_2$.

The resistivity response of a hemin-functionalized VDP sensors (Example 4) to NO, $NO_2$, and $O_2$ is shown in FIG. 11, using a protocol similar to that used in Example 6. For the InAs samples the functionalization significantly reduced the overall change in resistivity when exposed to low NO and $NO_2$ concentrations (ppm) as can be seen by comparing FIGS. 9 and 11. This attenuation was not observed in pre-functionalized samples that were repeatedly exposed to these analytes, and therefore appears to be caused by the respective elevated resistance baselines characteristic of the functionalized samples. Interestingly, the hemin-functionalized InAs had a 4.2% increase in resistivity response to $O_2$ compared to the negligible response of pre-functionalized InAs. This indicates a response due to the functional group is possibly in the form of an analyte-to-hemin binding event changing its dipole and reducing the free carrier concentration.

The hemin functional group did not appear to improve the selectivity of the semiconductors to NO. All three materials systems had little response to $O_2$ (which was introduced in orders of magnitude higher concentration than the other analytes) except for hemin-functionalized InAs. This selectivity of the bare-surfaces to NO and $NO_2$ over $O_2$ indicates that these semiconductor surfaces were sensitive to molecules with dipoles (with $NO_2$ having the largest dipole).

Figure 12:
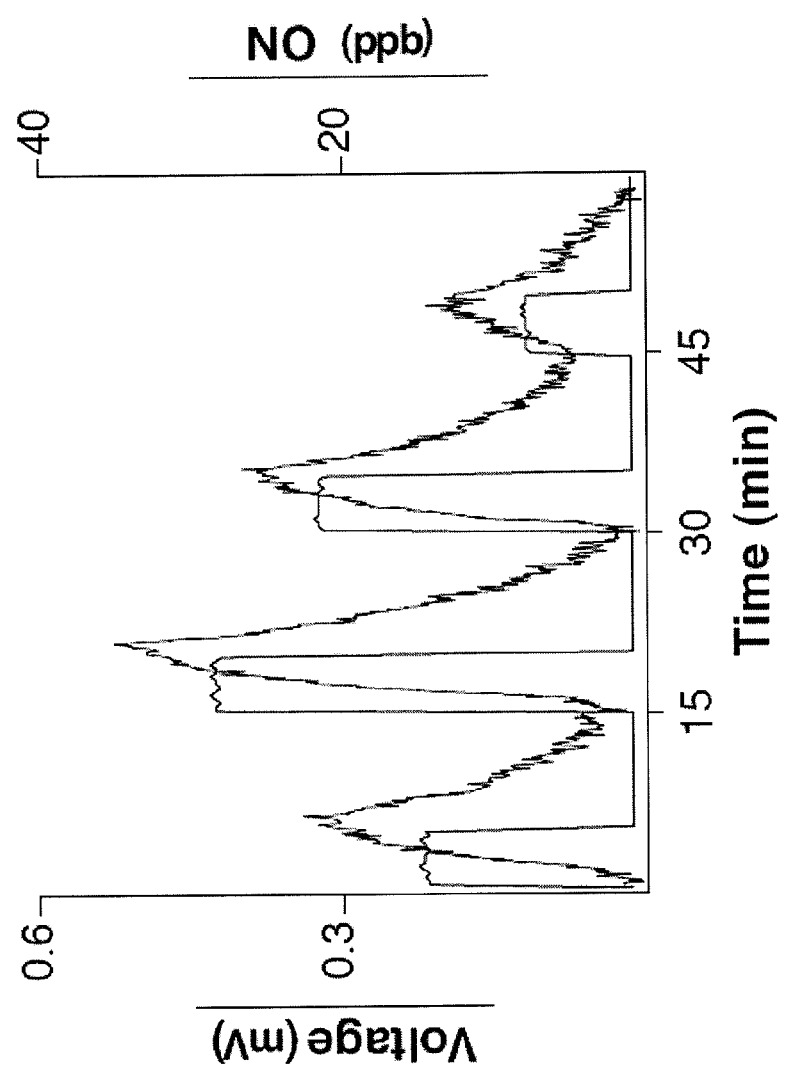
FIG. 12 shows the response of an embodiment of a van der Pauw sensor comprising an InAs surface functionalized with hemin and benzoic acid when exposed to NO.
Figure 13:
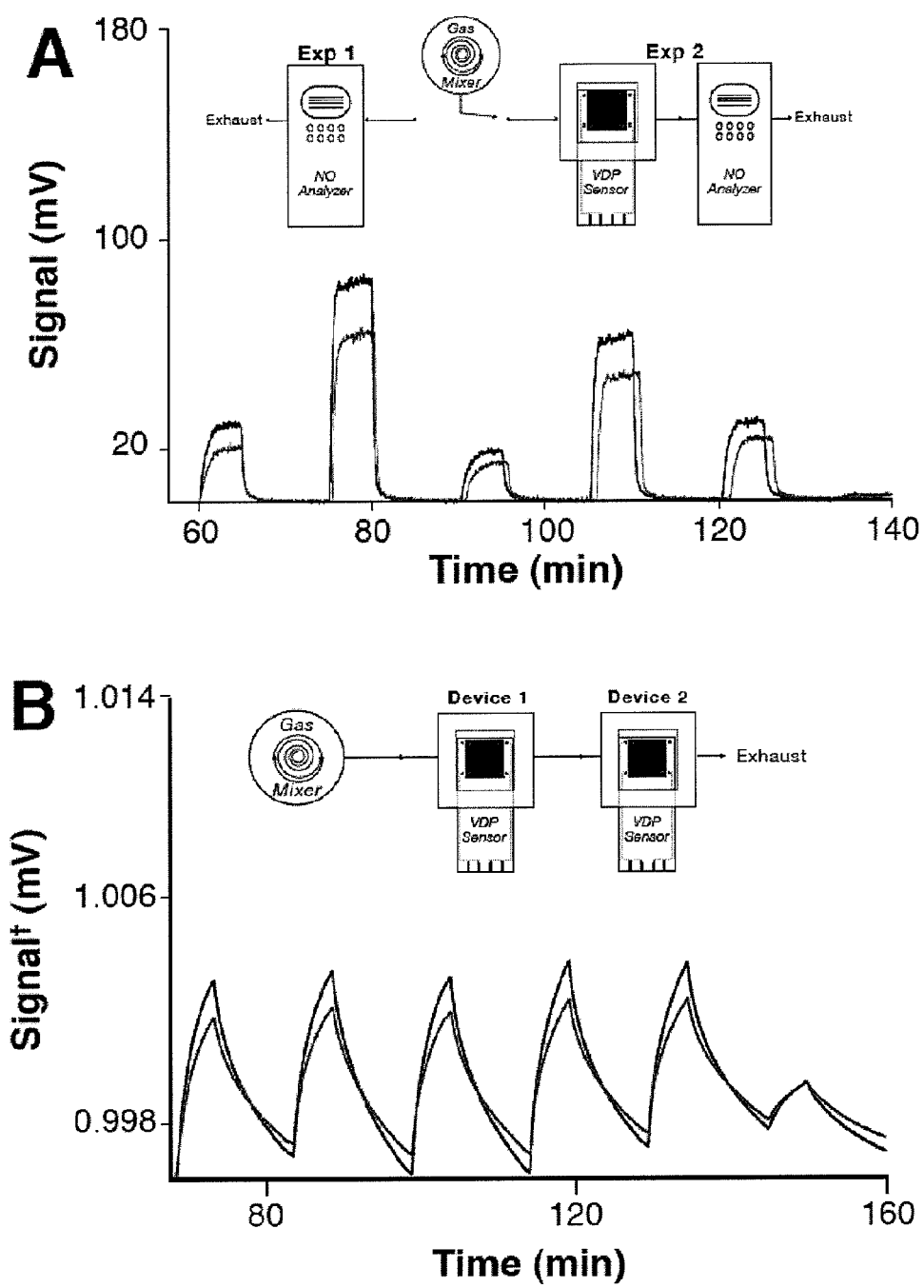
FIG. 13 A shows a paired measurement of an embodiment of a van der Pauw sensor comprising an InAs surface functionalized with hemin and a nitric acid analyzer.

Example 10—Time Response, Accuracy, and Reproducibility of Hemin-Functionalized InAs VDP Sensors As a further test of the robustness of the hemin-functionalized sensors made according to Example 4, additional tests were conducted to evaluate time response, accuracy, and reproducibility of the sensors. As shown in FIG. 12, the addition of hemin functionality (Example 2 versus Example 4) increased the responsiveness of the sensors to the introduction and removal of NO as monitored by the adjacent NO analyzer. In repeated tests, the hemin-functionalized sensors registered a measurable response to introduction of NO within seconds, and fell of after the maximum exposure to NO nearly immediately. The magnitude of the response of the hemin-functionalized sensors was also monitored concurrently with NO analyzers before and after the sensor as is shown in FIG. 13 A. As can be seen, the sensor exhibits a wide range of dynamic use, accurately following the results of the NO analyzers for concentrations of NO from ppb to parts-per-thousand levels. Finally, as can be seen in FIG. 13 B, two hemin-functionalized VDP sensors produced at different times maintain essentially the same functionality when exposed to NO.

Figure 14:
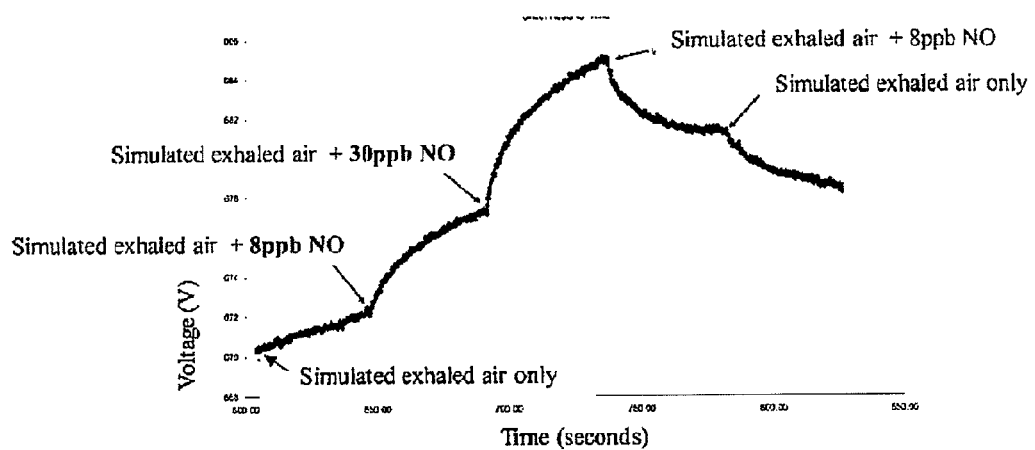
FIG. 14 shows an exemplary analysis of a simulated exhaled air sample with and without additional NO.

Example 11—Response of Hemin-Functionalized VDP Sensor to Simulated Exhaled Breath Having ppb Levels of Nitric Oxide A hemin-functionalized VDP sensor was constructed according to Example 4. The sensor was exposed to a simulated human exhaled breath, which comprised $CO_2$, $O_2$, $N_2$ and water vapor. The data shown in FIG. 14 was taken in simulated exhaled breath with varying levels of NO to highlight detection limit and sensitivity capabilities. The NO level of 8 ppb is above the detection limit and the sensitivity to changes in NO from 8 ppb to 30 ppb is evident. The level of increase simulates typical elevated levels of NO during an asthma attack.

Example 12—Multi-Porphyrin Functionalized Array of InAs VDP Sensors

Figure 15:
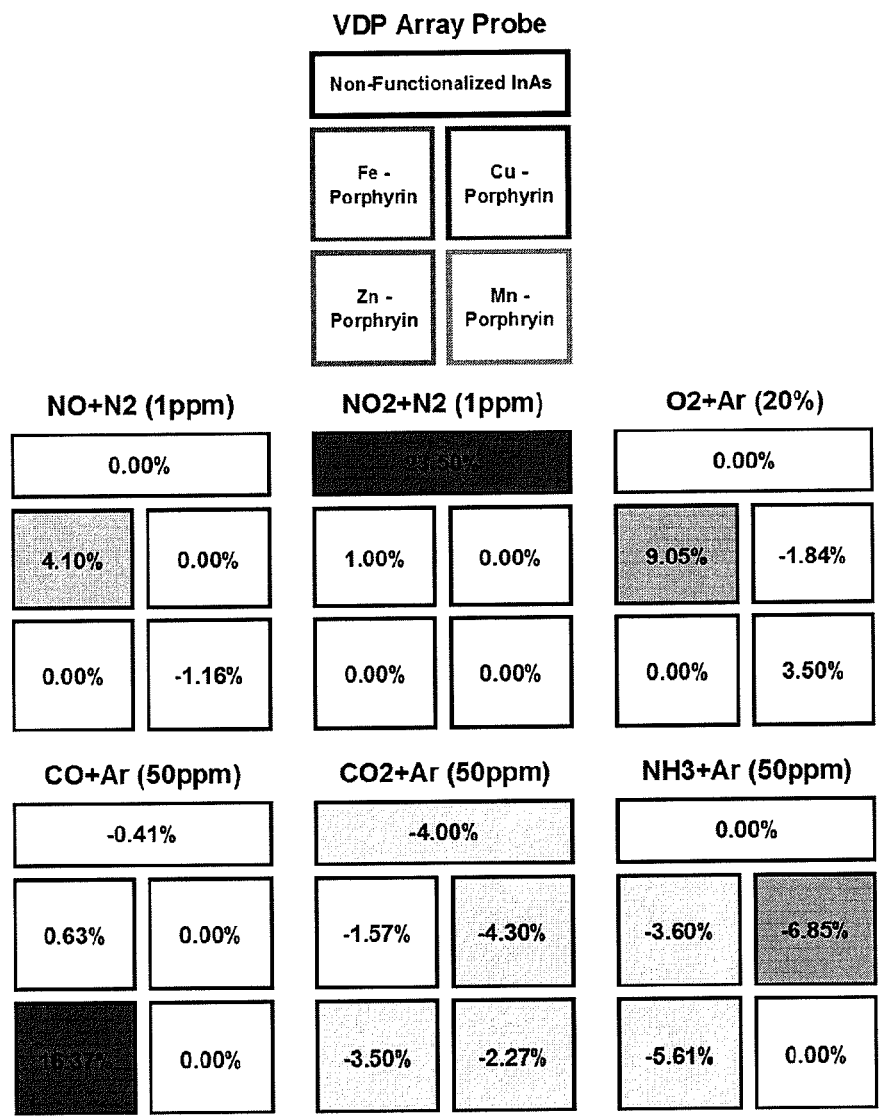
FIG. 15 shows a heat map response for an array of van der Pauw sensors comprising InAs surfaces without functionalization, and functionalized with multiple porphyrins, as the same array is exposed to different gasses.

An array of hemin functionalized n-InAs shows enhanced selectivity to NO, as indicated in FIG. 15, which shows fingerprint response for Fe—PP, Cu—PP, Zn-MP, and Mn—PP exposed to NO, $NO_2$, $O_2$, CO, $CO_2$, and $NH_3$ in background gases of either Ar or $N_2$. FIG. 15 shows a gray scale image of a conceptual 2×2 sensor array response to NO, $NO_2$, $O_2$ CO, $CO_2$, $NH_3$, and Oz in background gases of either Ar or $N_2$. The data is compared to bare, unfunctionalized response to each of the analyte—And highlights the effect of the porphyrins for targeted recognition. Four separate n-InAs VDP devices (Example 4) were functionalized with Fe—PP, Cu—PP, Zn-MP, and Mn—PP and the response to arbitrary levels of analytes was compared to that of an unfunctionalized VDP device (Example 2). In this case the data was collected by measuring the samples separately and constructing the response into the data array image. The data is informative in that it reveals characteristic selectivity to particular analyte (such as NO to Fe—PP) and both positive and negative $R_{SH}$ responses. Data analysis will be of interest for detect and quantify multiple analyte in variable gas mixtures with special emphasis on accurate NO measurement.

PROPHETIC EXAMPLES

Example 13—InN van der Pauw (VDP) Sensor

A VDP sensor, based on InN materials, will be fabricated as follows: A 1 cm×1 cm square of InN film will be mounted with double sided tape on a glass slide having electrical contacts bonded to the surface. (See, e.g., FIG. 4.) Gold wires will be bonded between the electrical connections and the four corners of the InN square with a solvent resistant epoxy. The resulting arrangement will allow for measurements of sheet resistivity of the InN square using the van der Pauw method. The connections between the InN square and the electrical connectors will be confirmed with a voltmeter. After electrical continuity is verified, the sensor will be cleaned with acetone and isopropyl alcohol, and then will be dried with $N_2$.

Example 14—InP van der Pauw (VDP) Sensor

A VDP sensor, based on InN materials, will be fabricated as follows: A 1 cm×1 cm square of InP film will be mounted with double sided tape on a glass slide having electrical contacts bonded to the surface. (See, e.g., FIG. 4.) Gold wires will be bonded between the electrical connections and the four corners of the InP square with a solvent resistant epoxy. The resulting arrangement will allow for measurements of sheet resistivity of the InP square using the van der Pauw method. The connections between the InP square and the electrical connectors will be confirmed with a voltmeter. After electrical continuity is verified, the sensor will be cleaned with acetone and isopropyl alcohol, and then will be dried with $N_2$.

Example 15—InN van der Pauw (VDP) Sensor

A second type of InN VDP sensor will be formed as follows: 40 nm of InN will be grown on a 1 cm×1 cm semi-insulating, Fe-doped InP substrate in a Riber 2300 molecular beam epitaxy (MBE) system. The buffer layer will be grown to reduce lattice mismatch at the InN/InP interface. In order to minimize the error for measurement of the material's electrical properties, four Ti/Au ohmic contacts will be applied to the corners of the sample, (See FIG. 4). The contacts will then be annealed in forming gas at 400° C. for 30 s. The arrangement of the contacts will allow for the calculation of the bulk sheet resistivity ($R_{SH}$) by applying current and measuring voltage from opposite pairs of contacts. The bulk sheet resistivity measurements will be performed in 8 different measurement configurations to provide a measure of $R_{SH}$.

The VDP devices will be attached to a printed circuit board and electronically connected with Au wire-bonds for sensor measurements. The surfaces of the samples will be degreased with acetone and isopropyl alcohol and dried with $N_2$ gas before testing.

Example 16—InN van der Pauw (VDP) Sensor with Functionalized Hemin and Benzoic Acid Spacers The InN VDP sensor of Example 15 will be further functionalized with hemin as follows: After the sheet resistivity response of the InN VDP sensor of Example 15 is verified as functional, the InN surface will be again degreased with brief ultrasonic scrubbing in solvents. A 1 mM hemin-Cl and benzoic acid (1:1) solution will be prepared in dimethylformamide (DMF), and the InN surface will be allowed to contact this solution for approximately 1 hr. After contacting the hemin/benzoic acid solution, the solution will be rinsed away with 5% v/v chloroformalhexane and the InN surface will be dried with Ar gas.

Example 17—Hemin Functionalized InAs VDP Sensors for the Detection of Asthma

A child suspected of having mild asthma will be evaluated as follows: An InAs-hemin functionalized VDP sensor will be constructed according to the methods of Example 4. A baseline for the sensor will be measured in an Ar environment. The sensor will then be exposed to a simulated human breath, comprising $CO_2$, $O_2$, $N_2$ and water vapor, to establish a baseline response to human breath. The sensor will then be passivated until the sensor returns to baseline for the Ar environment. The child will then breathe into a tube connected to the sensor to establish a baseline NO level. The sensor will then be passivated until the sensor returns to baseline for the Ar environment. The child will then endure mild exercise for 10 minutes and then again breathe into a tube connected to the sensor to determine if the NO level is elevated beyond an amount normal for a child of that age and weight. An elevated NO level will be indicative of an asthmatic condition in the child.

Example 18—Test for Exposure to Lead

A sample of human blood from a child suspected to have been exposed to lead will be tested for response to an InAs-porphyrin functionalized VDP sensor as follows: Two identical InAs-porphyrin functionalized VDP sensors will be constructed according to the methods of Example 4. In this example, however, the porphyrins are coproporphyrins without central metal atoms. Baseline responses for both sensors will be measured. The first sensor will be exposed to clean blood or a blood analogue. The second sensor will be exposed to the blood of a child suspected to have been exposed to lead. Because the higher lead concentration in the exposed child's blood will lead to a greater population of the coproporphyrins with lead in the second sensor, the second sensor will register a greater change in surface resistivity.

Example 19—Detection of Buried Explosives

An array of sensors similar to that discussed in Example 12 and shown in FIG. 15 will be constructed with a variety of unfunctionalized type III-V materials and a variety of type III-V materials functionalized with a range of porphyrin groups, including metalloporphyrins with varying metal centers. The array will be tested against a series of explosives known to be used in the construction of landmines in order to produce fingerprint signatures of the explosives. The sensor array will then be incorporated into a handheld device that can be used to detect buried landmines.

Thus, the invention provides, among other things, sensors for the detection of chemical species. Various features and advantages of the invention are set forth in the following claims.

What is claimed is:

1. A chemical sensor comprising an electronic circuit electrically coupled to a non-doped semiconductor material having a first edge and a second edge, the non-doped semi-conductor material comprising a type III-V material having a surface and a surface electron accumulation layer, and a macromolecule being in contact with the surface of the type III-V material such that binding of an analyte to the macromolecule causes a change in an electrical property of the type III-V material by altering the surface electron accumulation layer, the electronic circuit measuring the change in the electrical property of the type III-V material to detect binding of the analyte.

2. The chemical sensor of claim 1, wherein the type III-V material is in the shape of a surface, and the electronic circuit measures an electrical property of the surface.

3. The chemical sensor of claim 1, wherein the type III-V material comprises at least one of InAs, InN, and a combination thereof.

4. The chemical sensor of claim 1, wherein the electrical property is selected from the group consisting of resistivity, conductivity, capacitance, inductance, and impedance.

5. The chemical sensor of claim 1, wherein the macromolecule comprises at least one of a porphyrin, an oligonucleotide, a protein, a polymer or a combination thereof.

6. The chemical sensor of claim 5, wherein the macromolecule is a porphyrin.

7. The chemical sensor of claim 6, wherein the porphyrin comprises at least one of tetraphenyl porphyrin, a hemin, a corrin, a chlorin, a corphin, or a combination thereof.

8. The chemical sensor of claim 6, wherein the porphyrin has a central metal atom, and the central metal atom is selected from the group consisting of Fe, Co, Ni, Zn, Mg, Mn, Cu, Ru, V, Pb, and Cr.

9. The chemical sensor of claim 1, further comprising a spacer molecule contacting the sensor.

10. The chemical sensor of claim 9, wherein the spacer molecule is benzoic acid or a derivative of benzoic acid.

11. An array of chemical sensors, comprising multiple sensors of claim 1.

12. The array of chemical sensors of claim 11, wherein a first portion of the array of chemical sensors comprises porphyrins having a first central metal atom, and wherein a second portion of the array of chemical sensors comprises porphyrins having a second central metal atom, and wherein the first central metal atom and the second central metal atom are different.

13. The chemical sensor of claim 1, wherein the first edge of the semiconductor material is configured for applying current to said first edge and the second edge is configured for measuring voltage at said second edge to determine a first value of an electrical property of the semiconductor material.

14. A chemical sensor comprising an electronic circuit electrically coupled to a non-doped semiconductor material film supported on a substrate, the non-doped semi-conductor material comprising a type III-V material having a surface and a surface electron accumulation layer, and a macromolecule being in contact with the surface of the type III-V material such that binding of an analyte to the macromolecule causes a change in an electrical property of the type III-V material by altering the surface electron accumulation layer, the electronic circuit measuring the change in the electrical property of the type III-V material to detect binding of the analyte.

15. The chemical sensor of claim 14, wherein the semiconductor material film has a first edge and a second edge.

16. The chemical sensor of claim 15, wherein the first edge of the semiconductor material film is configured for applying current to said first edge and the second edge is configured for measuring voltage at said second edge to determine a first value of an electrical property of the semiconductor material film.

* * * * *